(12) United States Patent
Bannen et al.

(10) Patent No.: US 7,989,661 B2
(45) Date of Patent: Aug. 2, 2011

(54) HUMAN ADAM-10 INHIBITORS

(75) Inventors: Lynne Canne Bannen, Pacifica, CA (US); Erick W. Co, Redwood City, CA (US); Vasu Jammalamadaka, Pleasanton, CA (US); John M. Nuss, Danville, CA (US); Moon Hwan Kim, Palo Alto, CA (US); Donna Tra Le, San Jose, CA (US); Amy Lew, Milpitas, CA (US); Morrison B. Mac, San Francisco, CA (US); Shumeye Mamo, Berkeley, CA (US); Zhaoyang Wen, San Francisco, CA (US); Wei Xu, Danville, CA (US); Richard George Khoury, Redwood City, CA (US)

(73) Assignee: Symphony Evolution, Inc., Rockville, MD (US)

( * ) Notice: Subject to any disclaimer, the term of this patent is extended or adjusted under 35 U.S.C. 154(b) by 91 days.

(21) Appl. No.: 12/605,118

(22) Filed: Oct. 23, 2009

(65) Prior Publication Data
US 2010/0105953 A1      Apr. 29, 2010

Related U.S. Application Data

(62) Division of application No. 10/518,110, filed as application No. PCT/US03/18262 on Jun. 11, 2003, now Pat. No. 7,629,341.

(60) Provisional application No. 60/388,326, filed on Jun. 12, 2002.

(51) Int. Cl.
    C07C 309/09         (2006.01)
(52) U.S. Cl. .................. 562/828; 562/830; 562/833
(58) Field of Classification Search .................. None
    See application file for complete search history.

(56) References Cited

U.S. PATENT DOCUMENTS

| | | | |
|---|---|---|---|
| 4,213,775 A * | 7/1980 | Nagai et al. ........... | 504/302 |
| 5,215,549 A | 6/1993 | Hsu | |
| 5,380,525 A | 1/1995 | Leedle et al. | |
| 5,739,300 A | 4/1998 | Toepfer et al. | |
| 5,753,653 A | 5/1998 | Bender et al. | |
| 5,861,510 A | 1/1999 | Piscopio et al. | |
| 6,153,757 A | 11/2000 | Zook et al. | |
| 6,166,005 A | 12/2000 | De et al. | |
| 6,225,311 B1 | 5/2001 | Levin et al. | |
| 6,333,324 B1 | 12/2001 | Neya et al. | |
| 6,387,901 B1 | 5/2002 | Chupak | |
| 6,489,324 B2 | 12/2002 | Neya et al. | |
| 6,500,948 B1 | 12/2002 | Zook et al. | |
| 6,509,337 B1 | 1/2003 | Piscopio et al. | |
| 6,545,038 B1 | 4/2003 | De et al. | |
| 6,599,890 B1 | 7/2003 | McClure et al. | |
| 6,716,833 B2 | 4/2004 | Levin et al. | |
| 6,812,227 B2 | 11/2004 | Levin et al. | |
| 6,849,732 B2 | 2/2005 | Zook et al. | |
| 7,030,242 B2 | 4/2006 | Noe et al. | |
| 7,132,424 B2 | 11/2006 | Picard et al. | |
| 7,223,751 B2 | 5/2007 | Chung et al. | |
| 7,282,496 B2 | 10/2007 | Sandanayaka et al. | |
| 2003/0008849 A1 | 1/2003 | Levin et al. | |
| 2003/0060473 A1 | 3/2003 | Neya et al. | |
| 2003/0181441 A1 | 9/2003 | McClure et al. | |
| 2003/0186958 A1 | 10/2003 | De et al. | |
| 2004/0063672 A1 | 4/2004 | Frost et al. | |
| 2004/0106631 A1 | 6/2004 | Bernardelli et al. | |
| 2004/0229817 A1 | 11/2004 | Duggal et al. | |
| 2005/0113346 A1 | 5/2005 | Levin et al. | |
| 2005/0130958 A1 | 6/2005 | Li et al. | |
| 2005/0215549 A1 | 9/2005 | McClure et al. | |
| 2005/0282905 A1 | 12/2005 | Horiuchi | |
| 2006/0199820 A1 | 9/2006 | Bannen et al. | |
| 2007/0015207 A1 | 1/2007 | Ludovici et al. | |
| 2007/0142391 A1 | 6/2007 | Page et al. | |
| 2007/0155730 A1 | 7/2007 | Leit et al. | |

FOREIGN PATENT DOCUMENTS

| | | |
|---|---|---|
| CA | 2042571 | * 11/1991 |
| DE | 43 27 026 | 2/1995 |
| GB | 1 016 245 | 1/1966 |
| JP | 2000-247975 | 9/2000 |
| WO | 96/33172 | 10/1996 |
| WO | 97/20824 | 6/1997 |
| WO | 98/08825 | 3/1998 |
| WO | 98/27069 | 6/1998 |
| WO | 98/32748 | 7/1998 |
| WO | 98/34918 | 8/1998 |
| WO | 98/43963 | 10/1998 |
| WO | 99/58531 | 11/1999 |
| WO | 00/09492 | 2/2000 |

(Continued)

OTHER PUBLICATIONS

Feit et al., "Structure-activity studies on sulfamyl diuretics", Journal of Medicinal Chemistry, 15(4), 1972, 437-440.

Shahripour, A. B. et al., "Structure-based design of caspase—1 inhibitor containing a diphenyl ether sulfonamide", Biorganic & Medicinal Chemistry Letters, 11(20), 2001, 2779-2782.

Neale, A. J. et al., "Internuclear cyclizations of aromatic sulfonyl chlorides. Tribenz [b,d,f] oxepin and tribenzo [b,d,f] thiepin", Tetrahedron, 21(6), 1299-313., 1965.

Letavic et al., "Synthesis and biological activity of piperazine-based dual MMP-13 and TNF-alpha converting enzyme inhibitors", Bioorg. Med. Chem. Lett., 13(19), 2003, 3243-6.

Primary Examiner — Fiona T Powers
(74) Attorney, Agent, or Firm — McDonnell Boehnen Hulbert & Berghoff LLP

(57) ABSTRACT

The present invention provides compounds useful for inhibiting the ADAM-10 protein, with selectivity versus MMP-1. Such compounds are useful in the in vitro study of the role of ADAM-10 (and its inhibition) in biological processes. The present invention also comprises pharmaceutical compositions comprising one or more ADAM-10 inhibitors according to the invention in combination with a pharmaceutically acceptable carrier. Such compositions are useful for the treatment of cancer, arthritis, and diseases related to angiogenesis. Correspondingly, the invention also comprises methods of treating forms of cancer, arthritis, and diseases related to angiogenesis in which ADAM-10 plays a critical role.

10 Claims, No Drawings

FOREIGN PATENT DOCUMENTS

| | | |
|---|---|---|
| WO | 00/44709 | 8/2000 |
| WO | 01/55112 | 8/2001 |
| WO | 02/067866 | 9/2002 |
| WO | 02/083112 | 10/2002 |
| WO | 02/088115 | 11/2002 |
| WO | 03/037852 | 5/2003 |
| WO | 03/048142 | 6/2003 |
| WO | 03/051825 | 6/2003 |
| WO | 03/055851 | 7/2003 |
| WO | 03/057214 | 7/2003 |
| WO | 03/106381 | 12/2003 |
| WO | 2004/014892 | 2/2004 |
| WO | 2004/026818 | 4/2004 |
| WO | 2004/071390 | 8/2004 |
| WO | 2004/073599 | 9/2004 |
| WO | 2006/076442 | 7/2006 |
| WO | 2007/022638 | 3/2007 |
| WO | 2007/039736 | 4/2007 |

\* cited by examiner

HUMAN ADAM-10 INHIBITORS

This application is a divisional of U.S. patent application Ser. No. 10/518,110, filed Oct. 26, 2005, now U.S. Pat. No. 7,629,341, which is a US national phase of International Application PCT/US03/18262, filed Jun. 11, 2003, which claims priority to U.S. Provisional Application No. 60/388,326, filed Jun. 12, 2002, all of which are herein incorporated by reference in their entirety.

BACKGROUND OF THE INVENTION

1. Field of the Invention

The present invention is in the field of agents that inhibit human ADAM-10 (also known as human Kuzbanian) and their use in the treatment of cancer, arthritis, and diseases related to angiogenesis, such as renal diseases, heart diseases such as heart failure, atherosclerosis, and stroke, inflammation, ulcer, infertility, scleroderma, endometriosis, mesothelioma, and diabetes.

2. Summary of the Related Art

Cell-cell interactions play an important role in regulating cell fate decisions and pattern formation during the development of multicellular organisms. One of the evolutionarily conserved pathways that plays a central role in local cell interactions is mediated by the transmembrane receptors encoded by the Notch (N) gene of *Drosophila*, the lin-12 and glp-1 genes of *C. elegans*, and their vertebrate homologs (reviewed in Artavanis-Tsakonas, S., et al. (1995) Notch Signaling. Science 268, 225-232), collectively hereinafter referred to as NOTCH receptors. Several lines of evidence suggest that the proteolytic processing of NOTCH receptors is important for their function. For example, in addition to the full-length proteins, antibodies against the intracellular domains of NOTCH receptors have detected C-terminal fragments of 100-120 kd; see, e.g., Fehon, R. G., et al. (1990). Cell 61, 523-534; Crittenden, S. L., et al. (1994). Development 120, 2901-2911; Aster, J., et al. (1994) Cold Spring Harbor Symp. Quant. Biol. 59, 125-136; Zagouras, P., et al. (1995). Proc. Natl. Acad. Sci. U.S.A. 92, 6414-6418; and Kopan, R., et al. (1996). Proc. Natl. Acad. Sci. U.S.A. 93, 1683-1688. However, the mechanism(s) of NOTCH activation have been hitherto largely unknown.

During neurogenesis, a single neural precursor is singled out from a group of equivalent cells through a lateral inhibition process in which the emerging neural precursor cell prevents its neighbors from taking on the same fate (reviewed in Simpson, P. (1990). Development 109, 509-519). Genetic studies in *Drosophila* have implicated a group of "neurogenic genes" including N in lateral inhibition. Loss-of-function mutations in any of the neurogenic genes result in hypertrophy of neural cells at the expense of epidermis (reviewed in Campos-Ortega, J. A. (1993) In: The Development of *Drosophila melanogaster* M. Bate and A. Martinez-Arias, eds. pp. 1091-1129. Cold Spring Harbor Press.).

Rooke, J., Pan, D. J., Xu, T. and Rubin, G. M. (1996). Science 273, 1227-1231, discloses neurogenic gene family, kuzbanian (kuz). Members of the KUZ family of proteins are shown to belong to the recently defined ADAM family of transmembrane proteins, members of which contain both a disintegrin and metalloprotease domain (reviewed in Wolfsberg, T. G., et al. (1995). J. Cell Biol. 131, 275-278, see also Blobel, C. P., et al. (1992). Nature 356, 248-252, 1992; Yagami-Hiromasa, T., et al. (1995). Nature 377, 652-656; Black, R. A., et al. (1997). Nature 385, 729-733, 1997; and Moss, M. L., et al. (1997). Nature 385, 733-736; see also U.S. Pat. No. 5,922,546 and U.S. Pat. No. 5,935,792).

Genes of the ADAM family encode transmembrane proteins containing both metalloprotease and disintegrin domains (reviewed in Black and White, 1998 Curr. Opin. Cell Biol. 10, 654-659; Wolfsberg and White, 1996 Dev. Biol. 180, 389-401), and are involved in diverse biological processes in mammals such as fertilization (Cho et al., 1998 Science 281, 1857-1859), myoblast fusion (Yagami-Hiromasa et al., 1995 Nature 377, 652-656) and ectodomain shedding (Moss et al., 1997 Nature 385, 733-736; Black et al., 1997 Nature 385, 729-733; Peschon et al., 1998 Science 282, 1281-1284). The *Drosophila kuzbanian* (kuz) gene represents the first ADAM family member identified in invertebrates (Rooke et al., 1996 Science 273, 1227-1231). Previous genetic studies showed that kuz is required for lateral inhibition and axonal outgrowth during *Drosophila* neural development (Rooke et al., 1996; Fambrough et al., 1996 PNAS. USA 93, 13233-13238.; Pan and Rubin, 1997 Cell 90, 271-280; Sotillos et al., 1997 Development 124, 4769-4779). Specifically, during the lateral inhibition process, kuz acts upstream of Notch (Pan and Rubin, 1997; Sotillos et al., 1997), which encodes the transmembrane receptor for the lateral inhibition signal encoded by the Delta gene. More recently, a homolog of kuz was identified in *C. elegans* (SUP-17) that modulates the activity of a *C. elegans* homolog of Notch in a similar manner (Wen et al., 1997 Development 124, 4759-4767).

Vertebrate homologs of kuz have been isolated in *Xenopus*, bovine, mouse, rat and human. The bovine homolog of KUZ (also called MADM or ADAM 10) was initially isolated serendipitously based on its in vitro proteolytic activity on myelin basic protein, a cytoplasmic protein that is unlikely the physiological substrate for the bovine KUZ protease (Howard et al., 1996 Biochem. J. 317, 45-50). Expression of a dominant negative form of the murine kuz homolog (mkuz) in *Xenopus* leads to the generation of extra neurons, suggesting an evolutionarily conserved role for mkuz in regulating Notch signaling in vertebrate neurogenesis (Pan and Rubin, 1997). U.S. patent application. No. 09/697,854, to Pan et al., filed Oct. 27, 2000, discloses that mkuz mutant mice die around embryonic day (E) 9.5, with severe defects in the nervous system, the paraxial mesoderm and the yolk sac vasculature. In the nervous system, mkuz mutant embryos show ectopic neuronal differentiation. In the paraxial mesoderm, mkuz mutant embryos show delayed and uncoordinated segmentation of the somites. These phenotypes are similar to those of mice lacking Notch-1 or components of the Notch pathway such as RBP-Jk (Conlon et al, 1995, Development 121, 1533-1545; Oka et al., 1995), indicating a conserved role for mkuz in modulating Notch signaling in mouse development. Furthermore, no visible defect was detected in Notch processing in the kuz knockout animals. In addition to the neurogenesis and somitogenesis defect, mkuz mutant mice also show severe defects in the yolk sac vasculature, with an enlarged and disordered capillary plexus and the absence of large vitel-line vessels. Since such phenotype has not been observed in mice lacking Notch-1 or RBP-Jk (Swiatek et al., 1994 Genes Dev 15, 707-719; Conlon et al, 1995; Oka et al., 1995 Development 121, 3291-3301), Pan et al. determined that this phenotype reveals a novel function of mkuz that is distinct from its role in modulating Notch signaling, specifically, that kuz plays an essential role for an ADAM family disintegrin metalloprotease in mammalian angiogenesis.

In view of the important role of KUZ (ADAM-10) in biological processes and disease states, inhibitors of this protein are desirable, particularly small molecule inhibitors.

Studies have suggested that selective inhibition of matrix metalloproteases is important. A number of small molecule MMPI's have progressed into the clinic for cancer and rheumatoid arthritis, for example. Inhibition of MMP-1 has been implicated as the cause of side effects such as joint pain and tendonitis when unselective TACE inhibitors were employed (see Barlaam, B. et. Al. *J. Med. Chem.* 1999, 42, 4890). As well, clinical trials of broad spectrum inhibitors, such as "Marimastat," have been hampered due to musculoskeletal syndrome (MSS) which manifests as musculoskeletal pain after a few weeks treatment. Inhibition of MMP-1 has been suggested as having a role in the appearance of MSS. Recent efforts in the field have been directed toward design of "MMP-1 sparing" inhibitors; for example, BA-129566 emerged as a selective inhibitor which reportedly showed no signs of MSS in phase 2 clinical trials (see Natchus, M. G. et. Al. *J. Med. Chem.* 2000, 43, 4948).

Thus, what is needed are selective matrix metalloprotease inhibitors. Of particular use are selective ADAM-10 inhibitors, those that are "MMP-1 sparing."

All patents, applications, and publications recited herein are hereby incorporated by reference in their entirety.

SUMMARY OF THE INVENTION

The present invention provides compounds useful for inhibiting the ADAM-10 protein. Such compounds are useful in the in vitro study of the role of ADAM-10 (and its inhibition) in biological processes. The present invention also comprises pharmaceutical compositions comprising one or more ADAM-10 inhibitors according to the invention in combination with a pharmaceutically acceptable carrier. Such compositions are useful for the treatment of cancer, arthritis, and diseases related to angiogenesis, such as renal diseases, heart diseases such as heart failure, atherosclerosis, and stroke, inflammation, ulcer, infertility, scleroderma, endometriosis, mesothelioma, and diabetes. Correspondingly, the invention also comprises methods of treating forms of cancer, arthritis, and diseases related to angiogenesis in which ADAM-10 plays a critical role. In particular, the invention comprises inhibitors selective for ADAM-10, relative to MMP-1.

The foregoing merely summarizes certain aspects of the invention and is not intended to be limiting.

DETAILED DESCRIPTION OF THE INVENTION

The present invention comprises inhibitors of ADAM-10. In one embodiment, the invention comprises a compound of structural formula I:

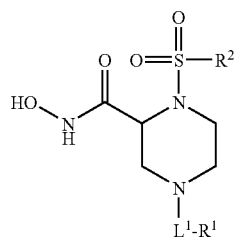

I and pharmaceutically acceptable salts, esters, amides, and prodrugs thereof wherein $L^1$ is —C(O)—, —S(O)$_2$—, or —(CH$_2$)$_n$—;
$R^1$ is —H, —OR$^{11}$, —(CH$_2$)$_n$R$^{11}$, —C(O)R$^{11}$, or —NR$^{12}$R$^{13}$;
$R^{11}$, $R^{12}$, and $R^{13}$ independently are
 a) $R^{50}$;
 b) saturated or mono- or poly-unsaturated $C_5$-$C_{14}$-mono- or fused poly-cyclic hydrocarbyl, optionally containing one or two annular heteroatoms per ring and optionally substituted with one or two $R^{50}$ substituents;
 c) $C_1$-$C_6$-alkyl, $C_2$-$C_6$-alkenyl, $C_2$-$C_6$-alkynyl, or —C(O)H, each of which is optionally substituted with one, two or three substituents independently selected from $R^{50}$ and saturated or mono- or poly-unsaturated $C_5$-$C_{14}$-mono- or fused poly-cyclic hydrocarbyl, optionally containing one or two annular heteroatoms per ring and optionally substituted with one, two or three $R^{50}$ substituents;
 or $R^{12}$ and $R^{13}$ together with the N to which they are covalently bound, a $C_5$-$C_6$ heterocycle optionally containing a second annular heteroatom and optionally substituted with one or two $R^{50}$ substituents;
$R^{21}$ is —$R^{21}$-$L^2$-$R^{22}$;
 $R^{21}$ is saturated or mono- or poly-unsaturated $C_5$-$C_{14}$-mono- or fused poly-cyclic hydrocarbyl, optionally containing one or two annular heteroatoms per ring and optionally substituted with one, two, or three $R^{50}$ substituents;
 $L^2$ is —O—, —C(O)—, —CH$_2$—, —NH—, —S(O$_2$)— or a direct bond;
 $R^{22}$ is saturated or mono- or poly-unsaturated $C_5$-$C_{14}$-mono- or fused poly-cyclic hydrocarbyl, optionally containing one or two annular heteroatoms per ring and optionally substituted with one, two, or three $R^{50}$ substituents; and
$R^{50}$ is $R^{51}$-$L^3$-(CH$_2$)$_n$—;
 $L^3$ is —O—, —NH—, —S(O)$_{0-2}$—, —C(O)—, —C(O)O—, —C(O)NH—, —OC(O)—, —NHC(O)—, —C$_6$H$_4$—, or a direct bond;
 $R^{51}$ is —H, $C_1$-$C_6$-alkyl, $C_2$-$C_6$-alkenyl, $C_2$-$C_6$-alkynyl, halo, —CF$_3$, —OCF$_3$, —OH, —NH$_2$, mono-$C_1$-$C_6$alkyl amino, di-$C_1$-$C_6$alkyl amino, —SH, —CO$_2$H, —CN, —NO$_2$, —SO$_3$H, or a saturated or mono- or poly-unsaturated $C_5$-$C_{14}$-mono- or fused poly-cyclic hydrocarbyl, optionally containing one or two annular heteroatoms per ring and optionally substituted with one, two, or three substituents;
wherein n is 0, 1, 2, or 3;
provided that an O or S is not singly bonded to another O or S in a chain of atoms.

In one example, according to paragraph [0013], $L^1$ is —C(O)— or —S(O)$_2$—.

In another example, according to paragraph [0014], $L^1$ is —C(O)— and $R^1$ is —OR$^{11}$ or —(CH$_2$)$_n$R$^{11}$, —OC$_1$-$C_6$alkyl-mono-$C_1$-$C_6$alkyl amino, —OC$_1$-$C_6$alkyl-di-$C_1$-$C_6$alkyl amino, —OC$_1$-$C_6$alkyl-N-heterocyclyl, —C$_1$-$C_6$alkyl-mono-$C_1$-$C_6$alkyl amino, —$C_1$-$C_6$alkyl-di-$C_1$-$C_6$alkyl amino, or —$C_1$-$C_6$alkyl-N-heterocyclyl. In a more specific example, $R^1$ is $C_1$-$C_6$-alkoxy-$C_1$-$C_6$-alkoxy; and in a still more specific example $R^1$ is methoxyethoxy.

In another example, according to paragraph [0015], $L^1$ is —S(O)$_2$—, and $R^1$ is —NR$^{12}$R$^{13}$, —(CH$_2$)$_n$R$^{11}$, amino, —$C_1$-$C_6$alkyl-di-$C_1$-$C_6$alkyl amino, or —$C_1$-$C_6$alkyl-N-heterocyclyl.

In another example, according to paragraph [0015] or [0016], $L^2$ is —O—.

In another example, according to paragraph [0017], $R^2$ is phenoxyphenyl wherein each phenyl is optionally substituted with one or two $R^{50}$ substituents. In a more specific example, the $R^{50}$ substituents are halo.

In another example, according to paragraph [0018], the saturated or mono- or poly-unsaturated $C_5$-$C_{14}$-mono- or fused poly-cyclic hydrocarbyl containing one or two annular heteroatoms per ring is selected from the group consisting of morpholinyl, piperazinyl, homopiperazinyl, pyrrolidinyl, piperidinyl, homopiperidinyl, furyl, thienyl, pyranyl, isobenzofuranyl, chromenyl, pyrrolyl, imidazolyl, isoxazolyl, pyridyl, pyrazinyl, pyrimidinyl, oxadiazolyl, indolyl, quinolinyl, carbazolyl, acridinyl, and furazanyl, optionally substituted with one or two $R^{50}$ substituents.

In another example, according to paragraph [0018], $R^{12}$ and $R^{13}$, together with the N to which they are covalently bound, form a heterocycle selected from the group consisting of morpholinyl, piperazinyl, homopiperazinyl, pyrrolidinyl, piperidinyl, homopiperidinyl, pyrrolyl, imidazolyl, isoxazolyl, pyridyl, pyrazinyl, pyrimidinyl, oxadiazolyl, indolyl, quinolinyl, carbazolyl, acrydinyl, and furazanyl, optionally substituted with one or two $R^{50}$ substituents.

In another example, the compound is according to paragraph [0013], having the absolute stereochemistry of structural formula II:

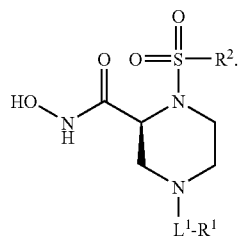

II

In another example, the compound is according to paragraph [0013], having the absolute stereochemistry of structural formula III:

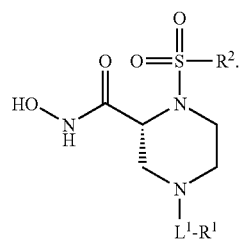

III

In another example, the compound of the invention is according to paragraph [0013], wherein -$L^1$-$R^1$ is selected from Table 1;

TABLE 1

TABLE 1-continued
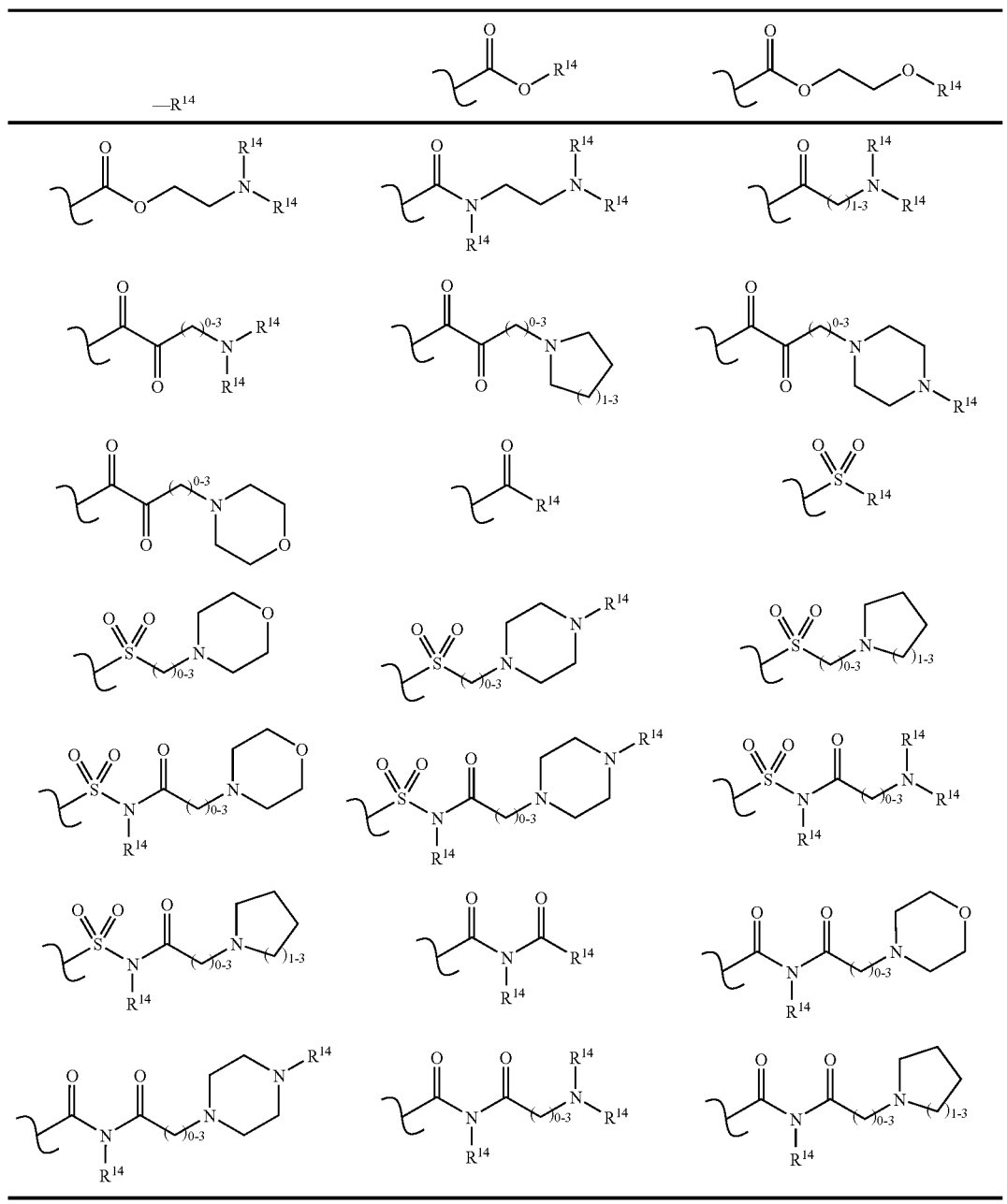
wherein each $R^{14}$ is independently selected from —H, —$(CH_2)_{1-3}CO_2H$, alkyl, alkoxy, alkenyl, aryl, heteroaryl, arylalkyl, and heteroarylalkyl;
and $R^2$ is selected from Table 2;
TABLE 2
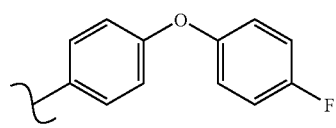
TABLE 2-continued
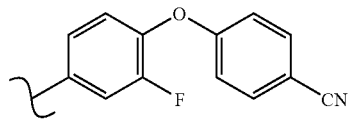
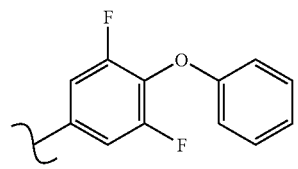

TABLE 2-continued
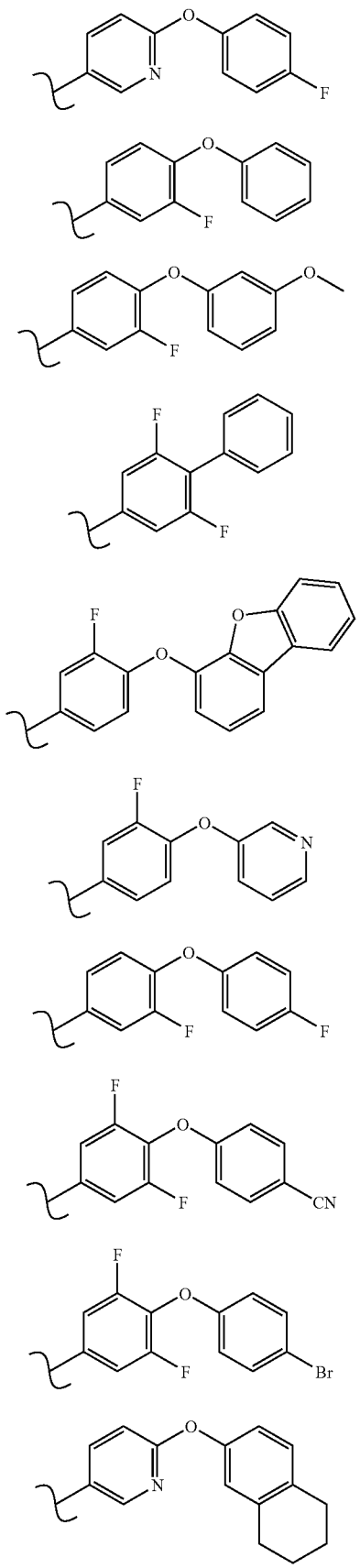
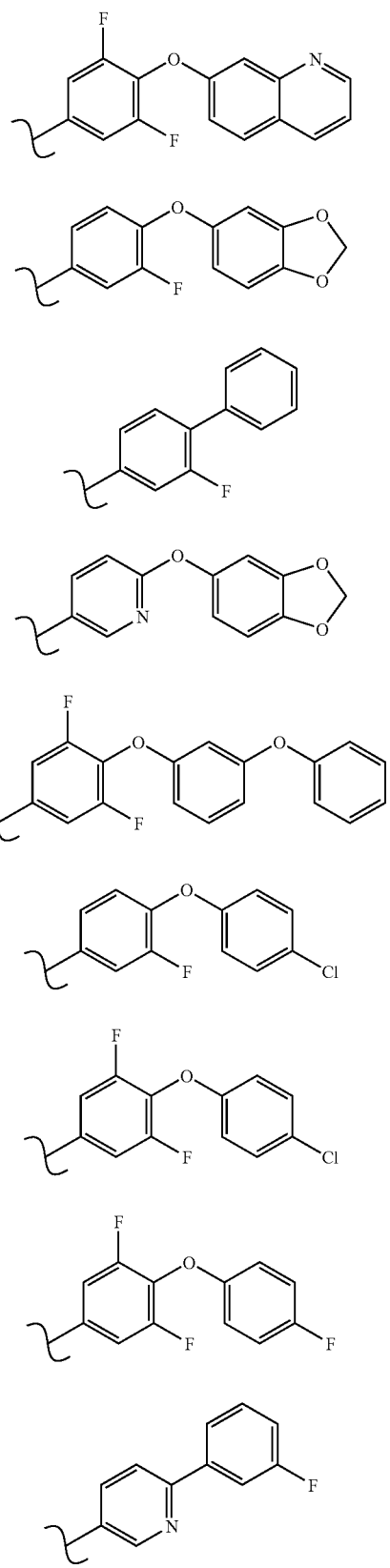

TABLE 2-continued
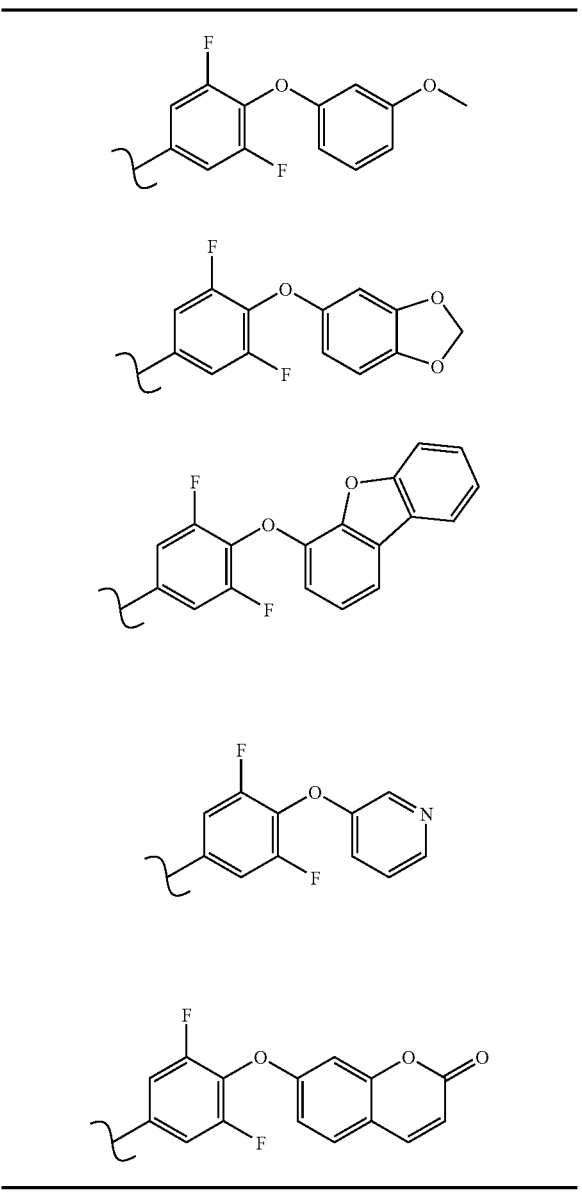
In another example the compound is according to paragraph [0013], selected from Table 3:
TABLE 3
TABLE 3-continued
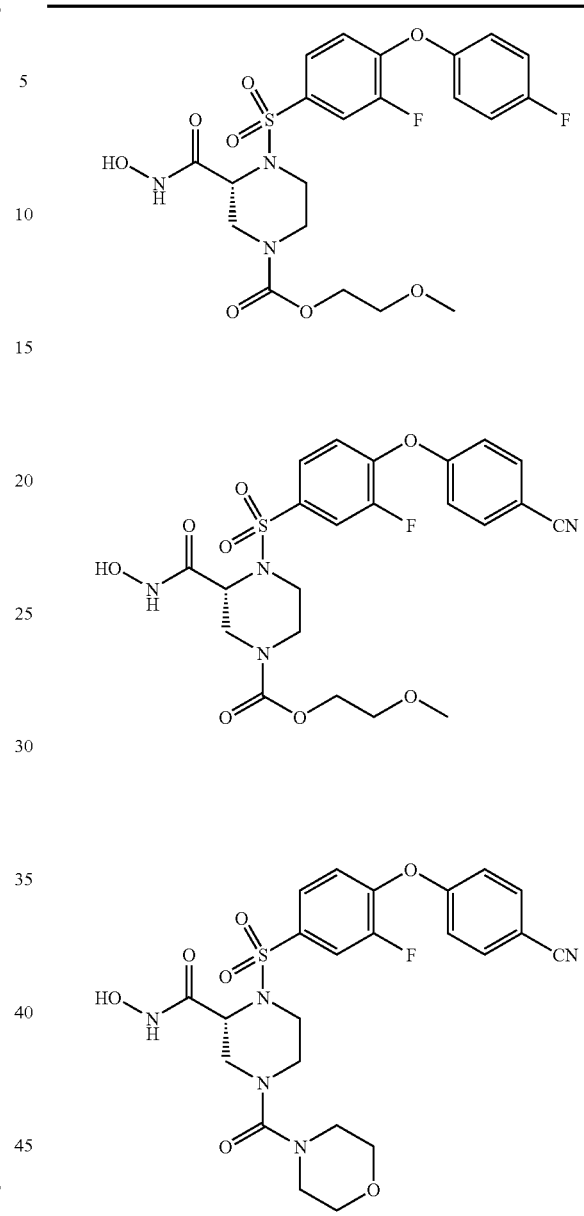
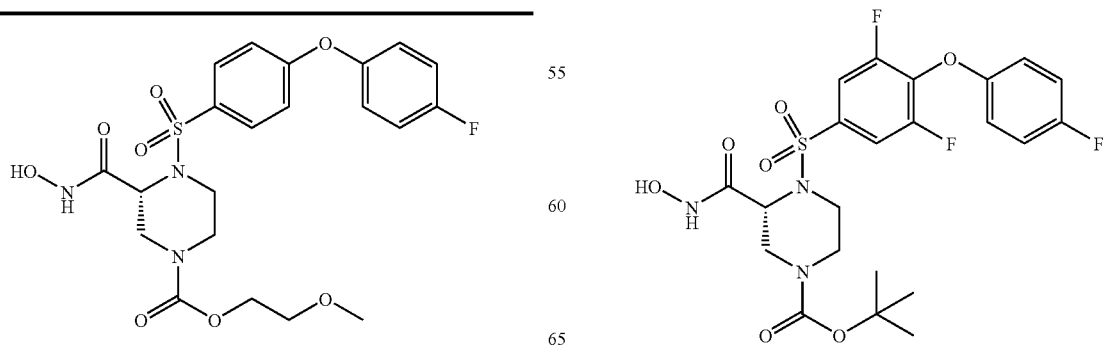

TABLE 3-continued
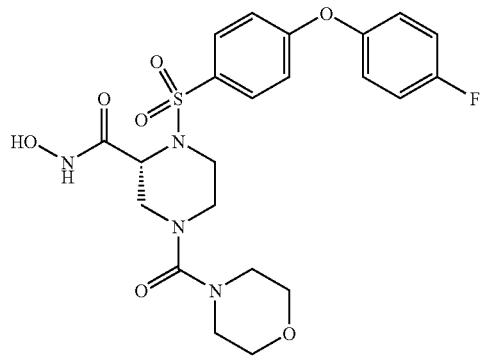
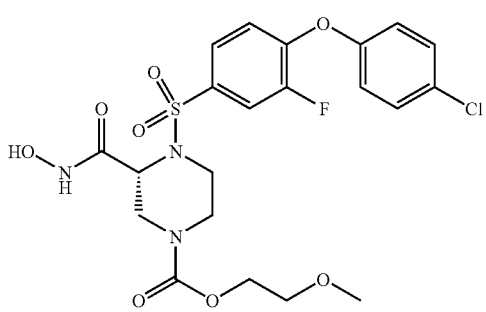
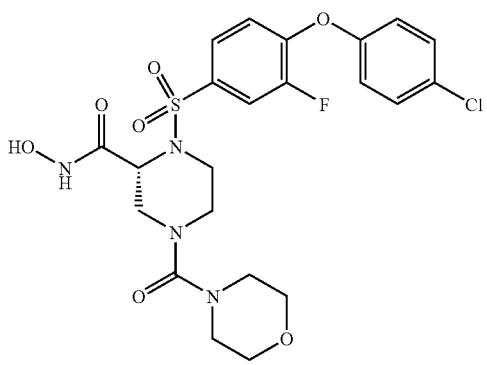
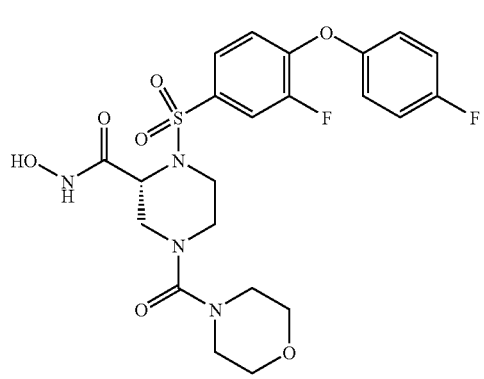
TABLE 3-continued
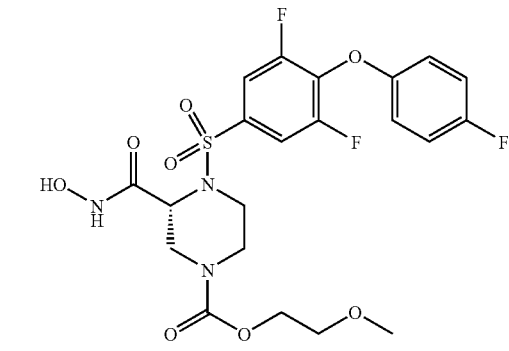
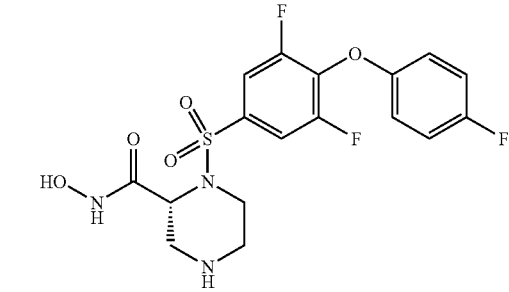
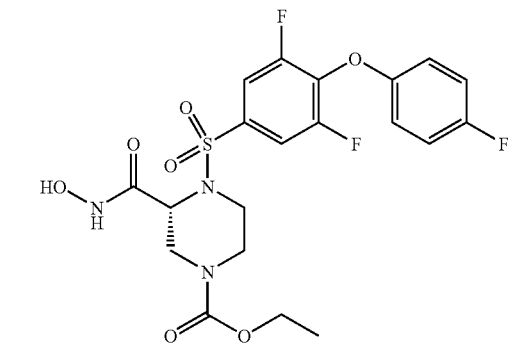
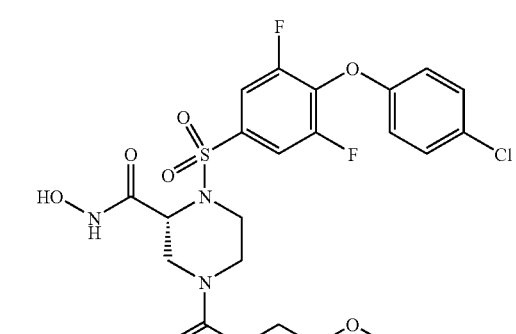

TABLE 3-continued
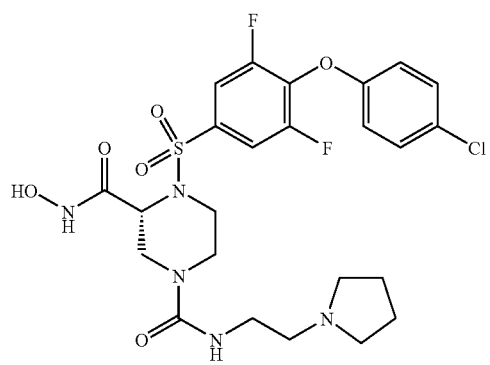
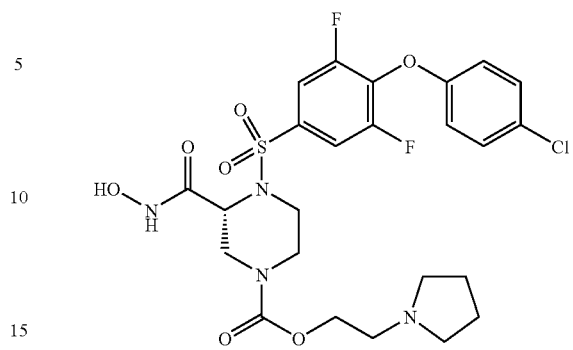
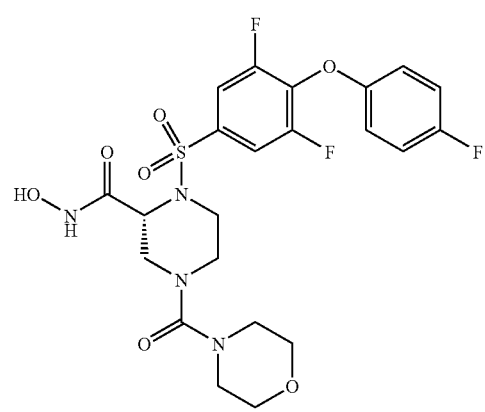
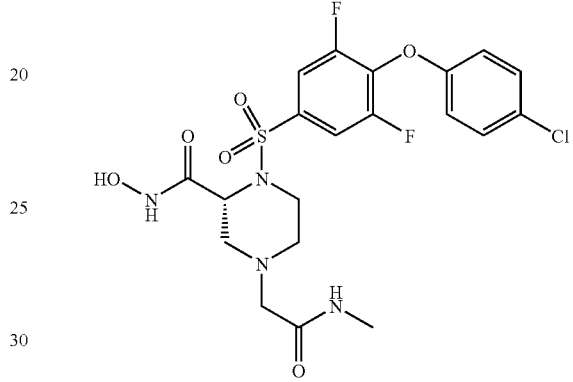
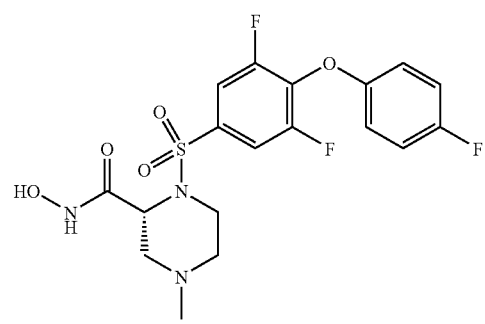
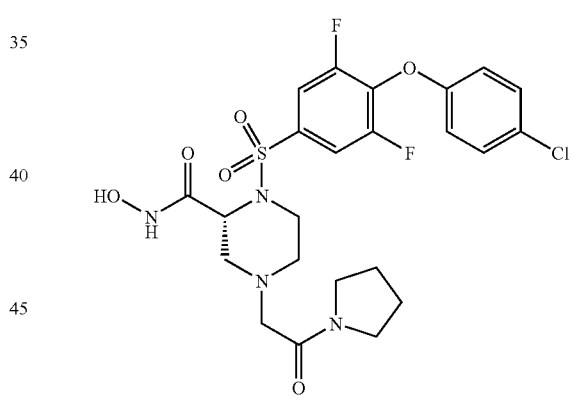
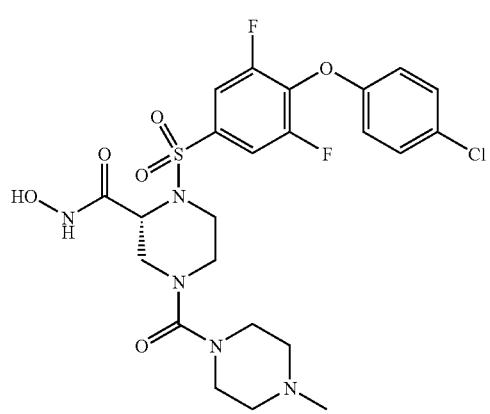
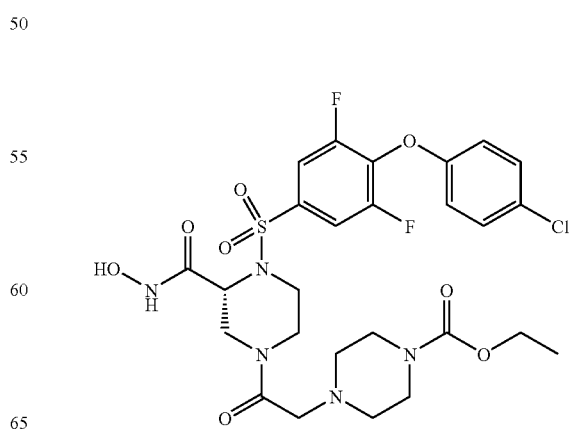

TABLE 3-continued
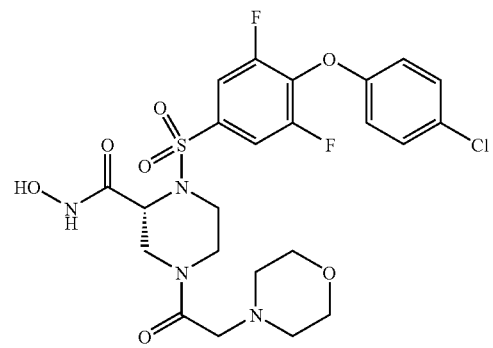
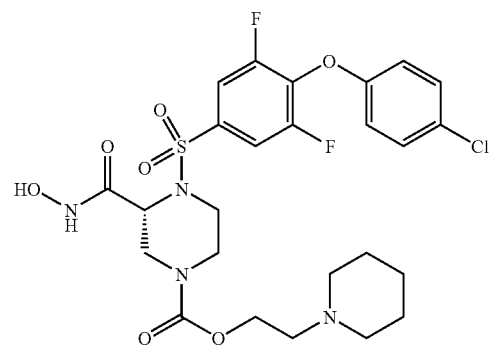
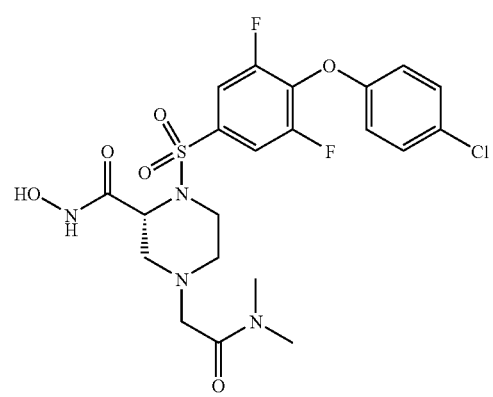
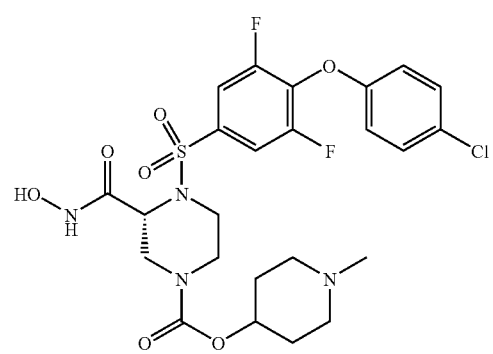
TABLE 3-continued
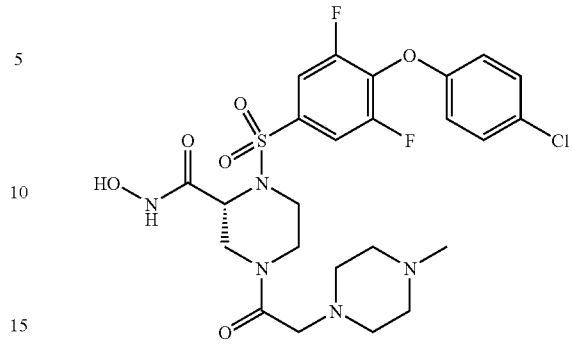
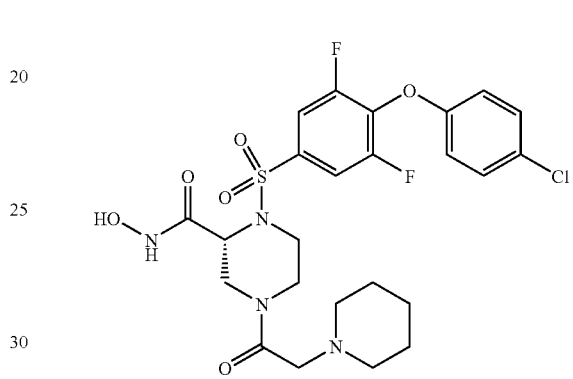
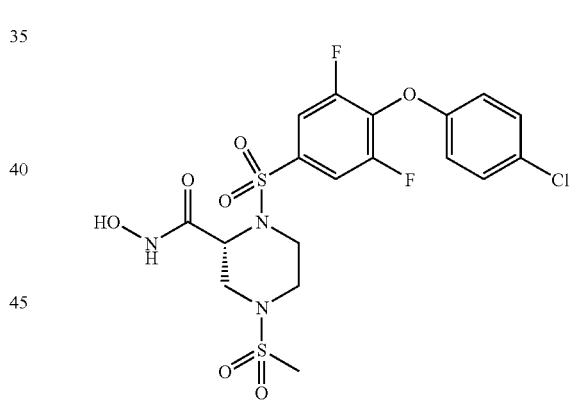
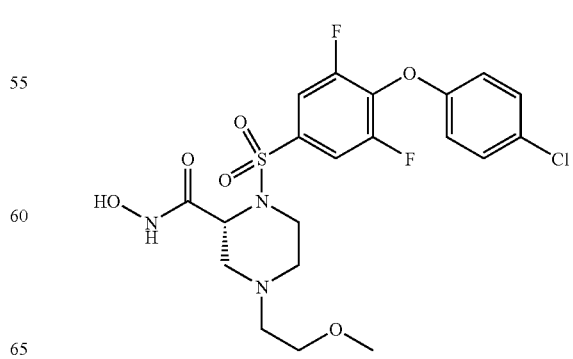

TABLE 3-continued
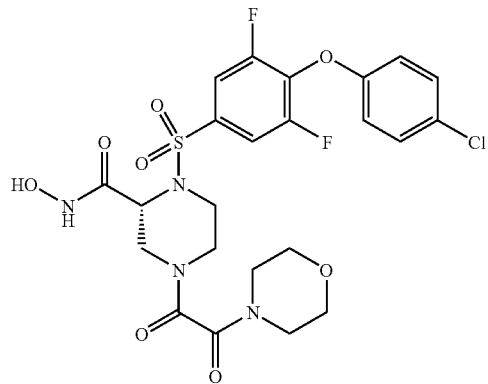
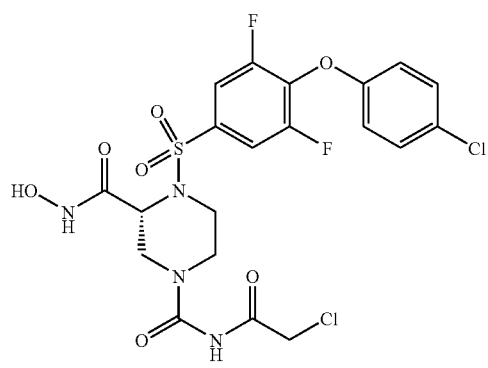
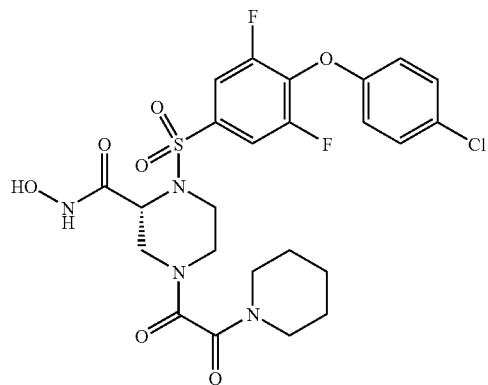
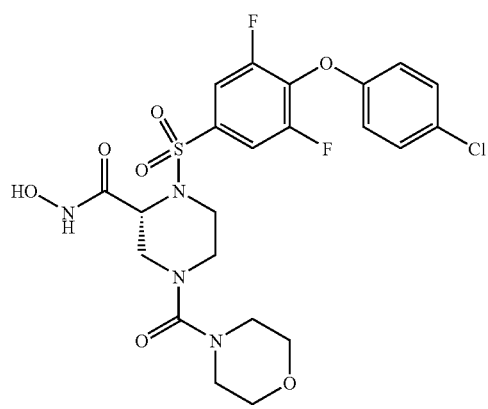
TABLE 3-continued
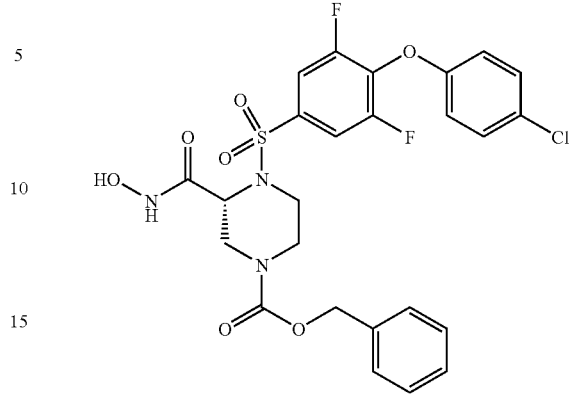
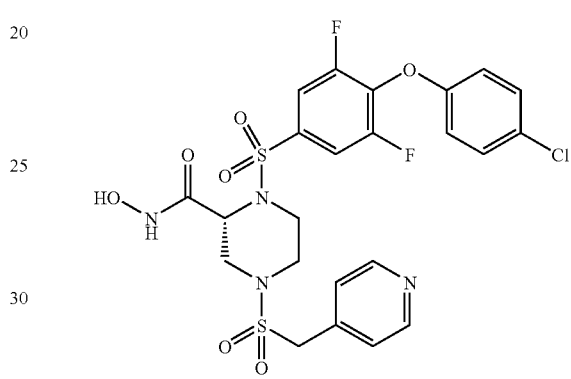
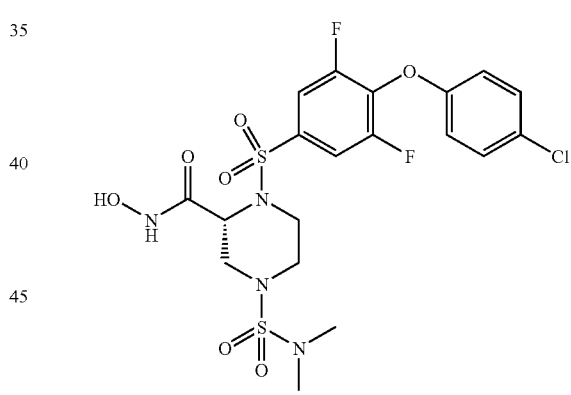
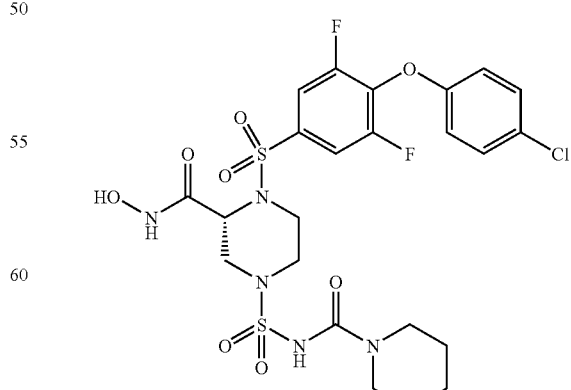

TABLE 3-continued
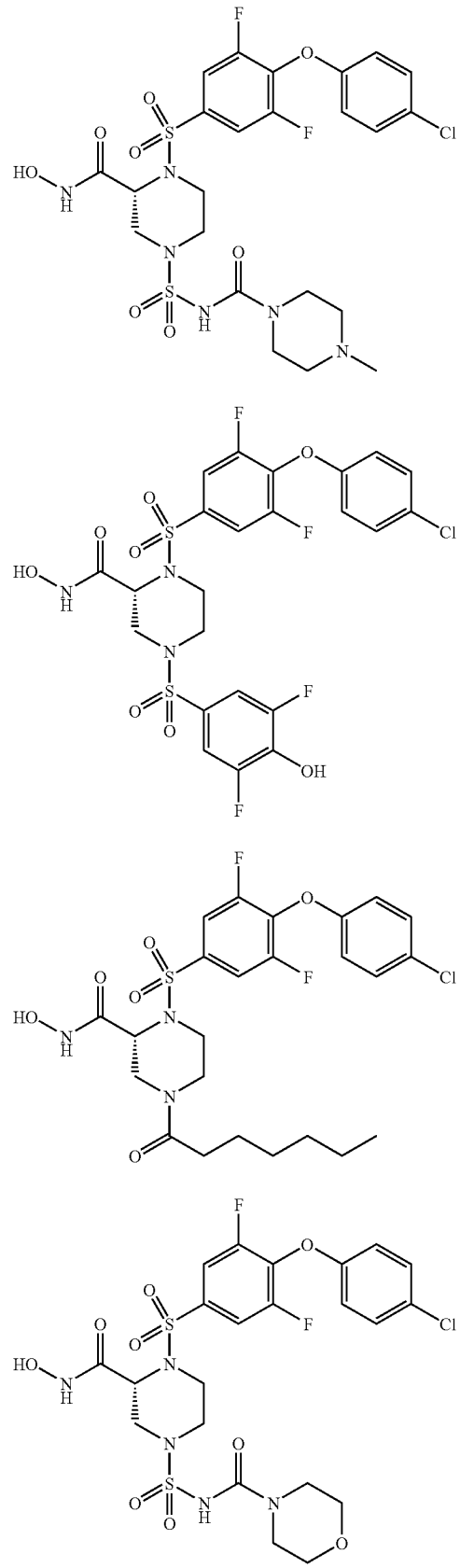
TABLE 3-continued
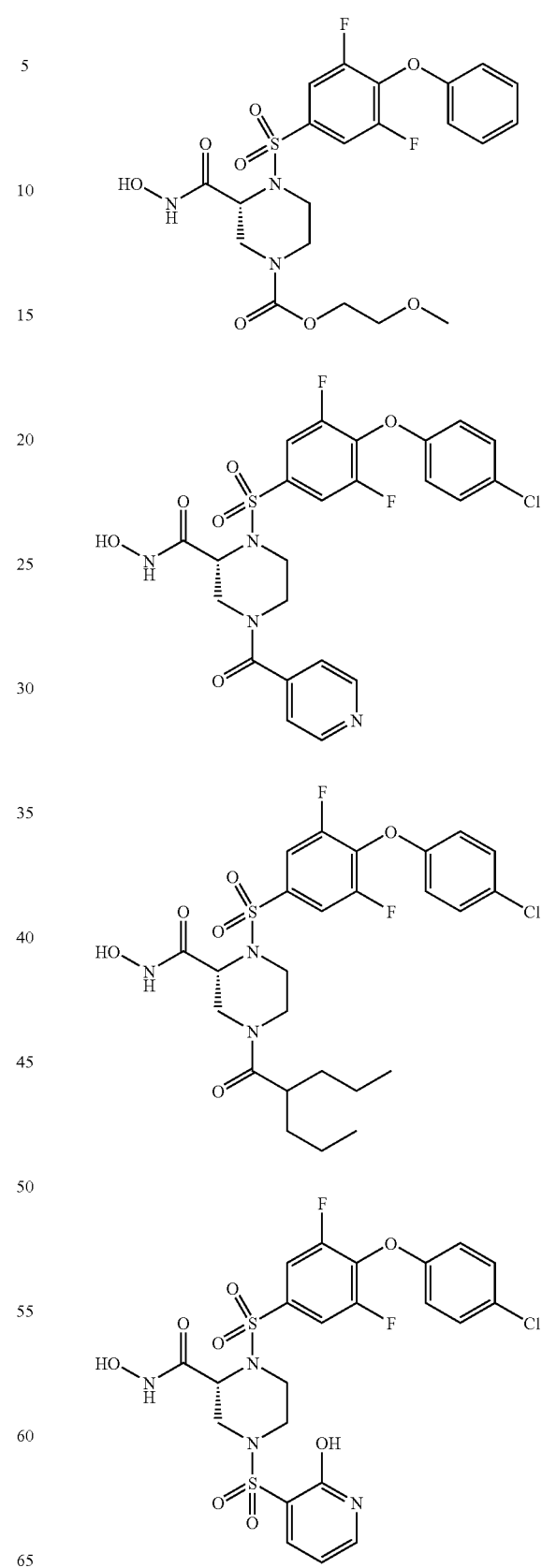

TABLE 3-continued
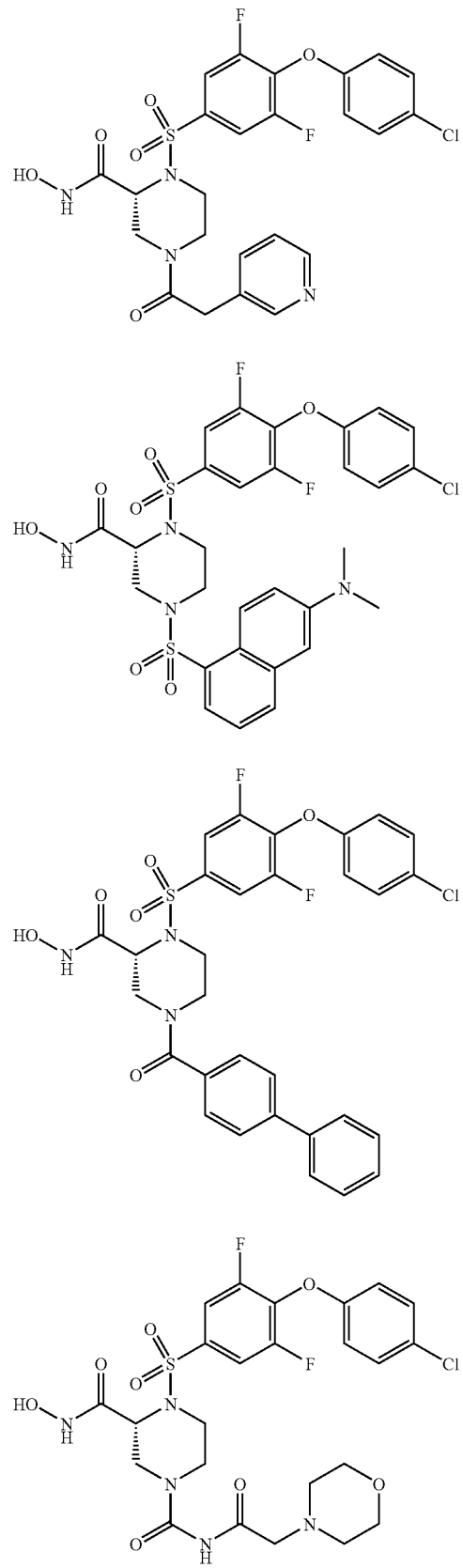
TABLE 3-continued
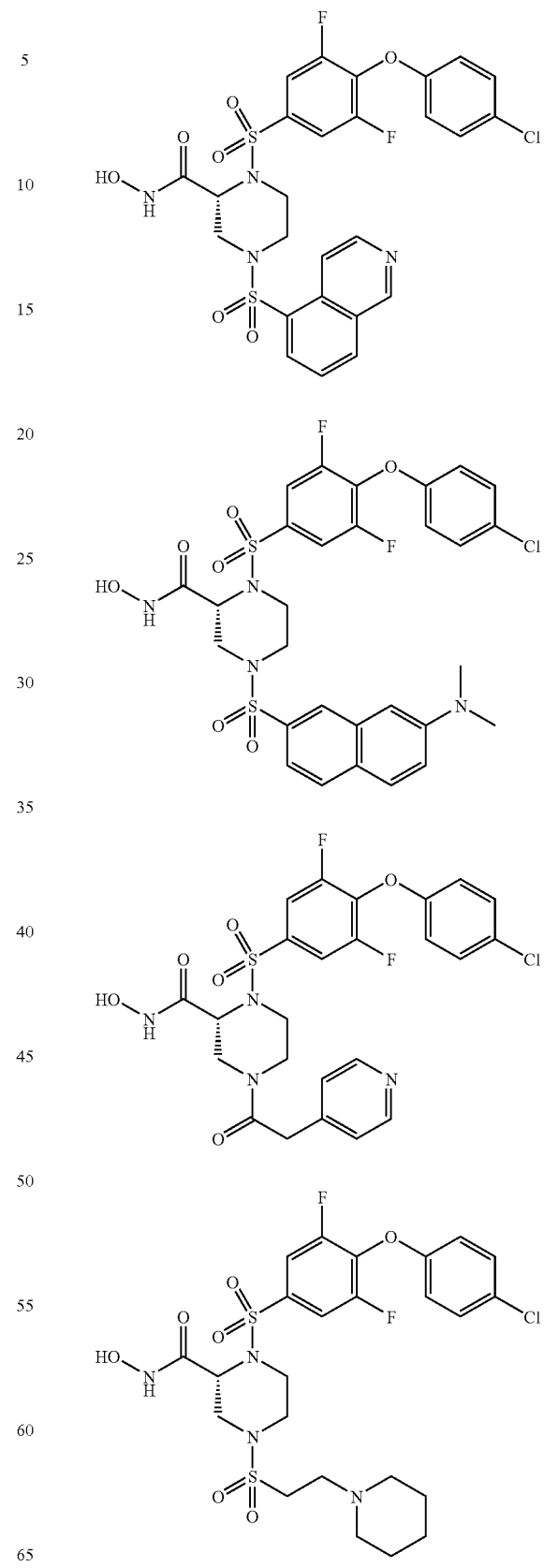

TABLE 3-continued
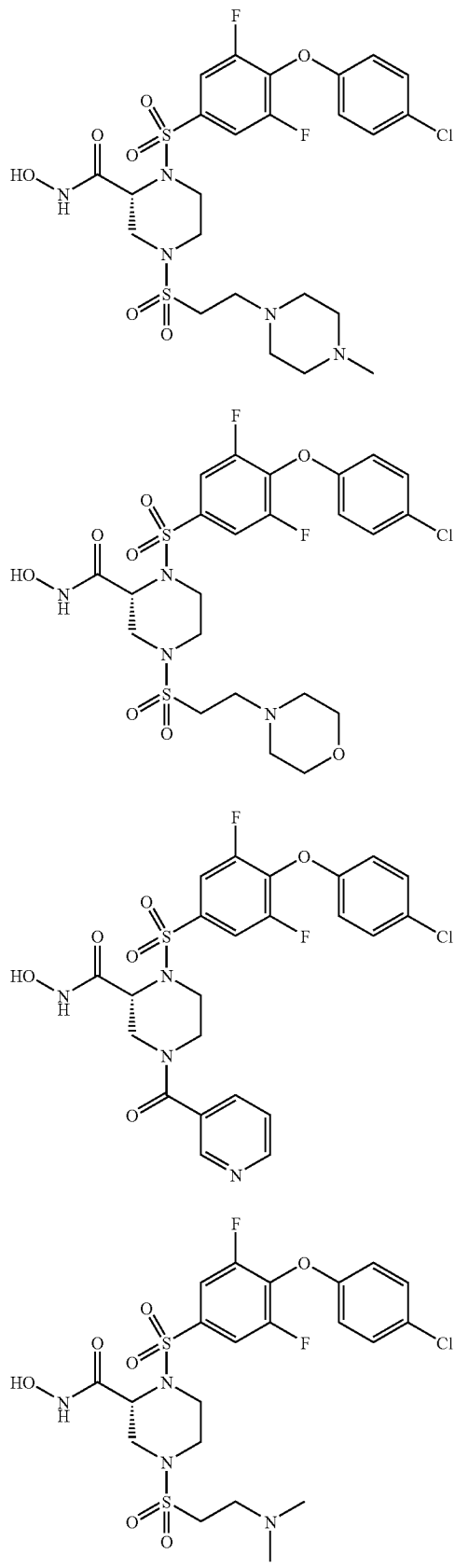
TABLE 3-continued
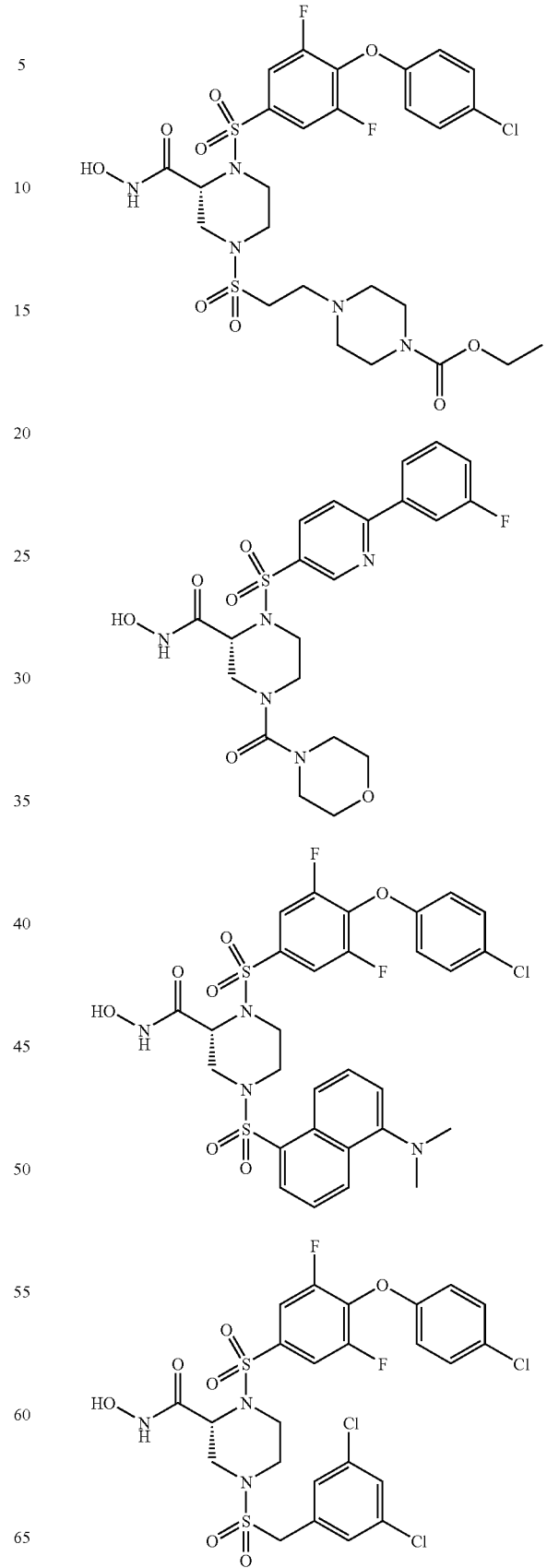

TABLE 3-continued

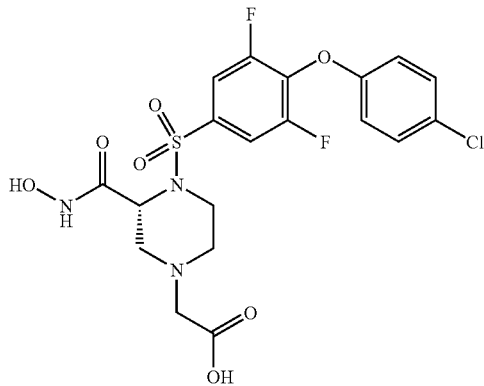

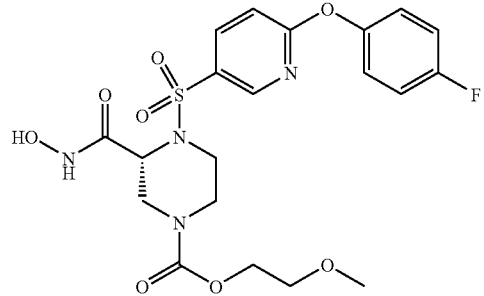

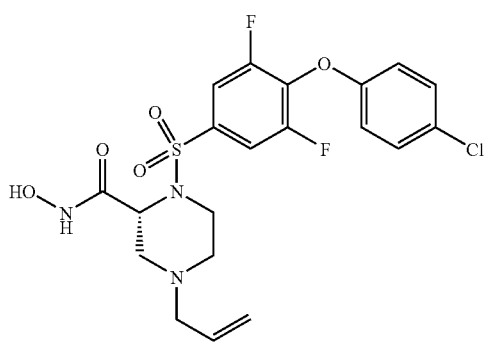

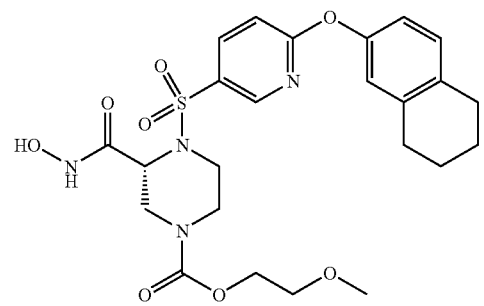

TABLE 3-continued

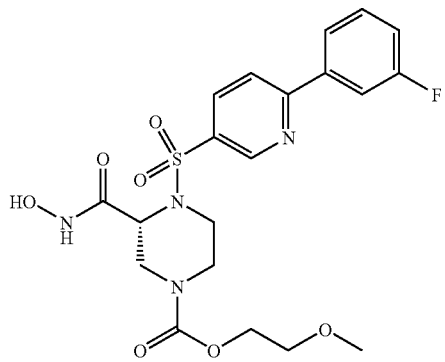

In another aspect, the invention comprises compounds according to formula IV,

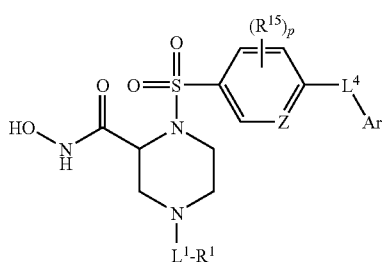

IV and pharmaceutically acceptable salts, esters, amides, and prodrugs thereof wherein,
Z is —C(R$^{15}$)=, —C(H)=, or —N=;
Ar is aryl or heteroaryl, each optionally substituted;
R$^{15}$ is fluoro;
p is 0, 1, 2, or 3;
L$^1$ is —C(O)—, —S(O)$_2$—, or —(CH$_2$)$_n$—;
L$^4$ is nothing or —O—;
R$^1$ is —H, —OR$^{11}$, —(CH$_2$)$_n$R$^{11}$, —C(O)R$^{11}$, or —NR$^{12}$R$^{13}$;
  R$^{11}$, R$^{12}$, and R$^{13}$ independently are
    d) R$^{50}$;
    e) saturated or mono- or poly-unsaturated C$_5$-C$_{14}$-mono- or fused poly-cyclic hydrocarbyl, optionally containing one or two annular heteroatoms per ring and optionally substituted with one or two R$^{50}$ substituents;
    f) C$_1$-C$_6$-alkyl, C$_2$-C$_6$-alkenyl, C$_2$-C$_6$-alkynyl, or —C(O)H, each of which is optionally substituted with one, two or three substituents independently selected from R$^{50}$ and saturated or mono- or poly-unsaturated C$_5$-C$_{14}$-mono- or fused poly-cyclic hydrocarbyl, optionally containing one or two annular heteroatoms per ring and optionally substituted with one, two or three R$^{50}$ substituents;
    or R$^{12}$ and R$^{13}$ together with the N to which they are covalently bound, a C$_5$-C$_6$ heterocycle optionally containing a second annular heteroatom and optionally substituted with one or two R$^{50}$ substituents; and
R$^{50}$ is R$^{51}$-L$^3$-(CH$_2$)$_n$—;
  L$^3$ is —O—, —NH—, —S(O)$_{0-2}$—, —C(O)—, —C(O)O—, —C(O)NH—, —OC(O)—, —NHC(O)—, —C$_6$H$_4$—, or a direct bond;

$R^{51}$ is —H, $C_1$-$C_6$-alkyl, $C_2$-$C_6$-alkenyl, $C_2$-$C_6$-alkynyl, halo, —$CF_3$, —$OCF_3$, —OH, —$NH_2$, mono-$C_1$-$C_6$alkyl amino, di-$C_1$-$C_6$alkyl amino, —SH, —$CO_2H$, —CN, —$NO_2$, —$SO_3H$, or a saturated or mono- or poly-unsaturated $C_5$-$C_{14}$-mono- or fused poly-cyclic hydrocarbyl, optionally containing one or two annular heteroatoms per ring and optionally substituted with one, two, or three substituents;

wherein n is 0, 1, 2, or 3;

provided that an O or S is not singly bonded to another O or S in a chain of atoms.

In one example the compound is according to paragraph [0025], wherein -$L^1$-$R^1$ is selected from Table 4,

TABLE 4

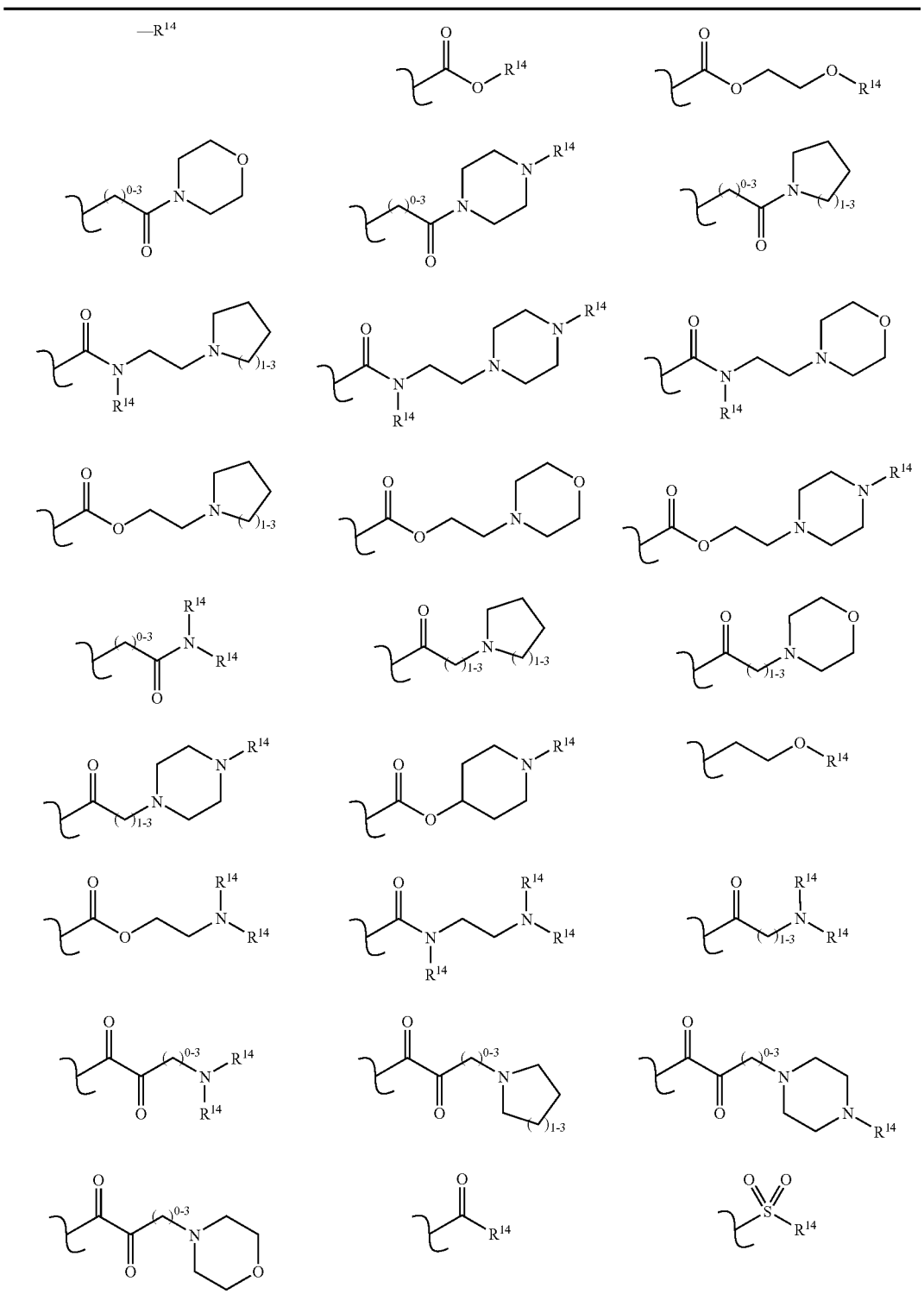

TABLE 4-continued

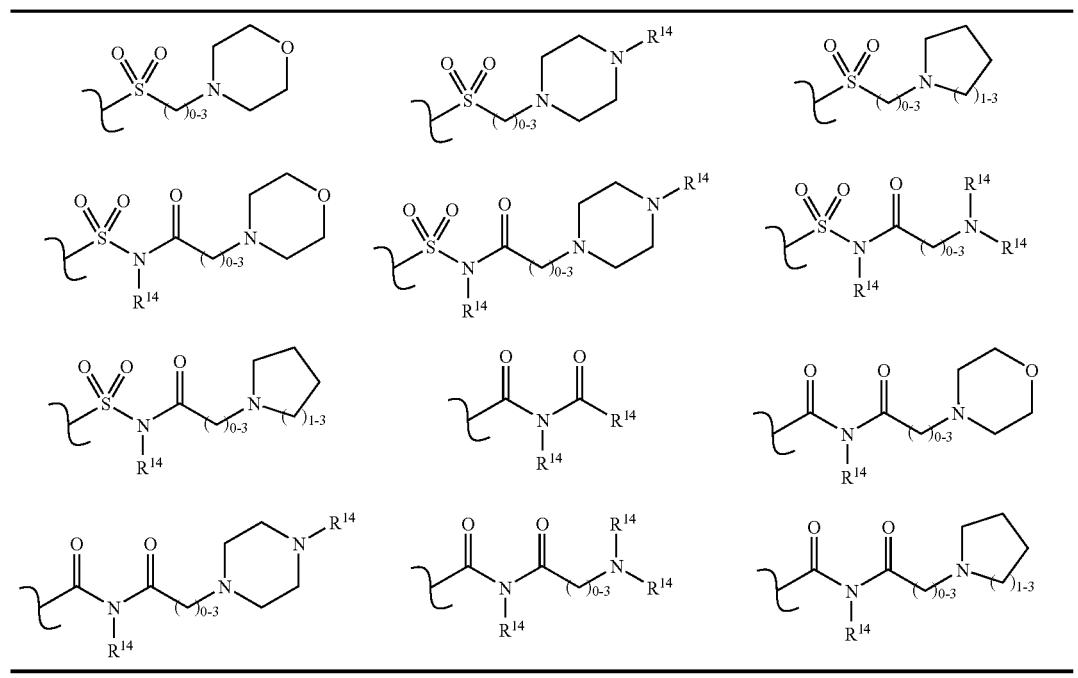

wherein each $R^{14}$ is independently selected from —H, —$(CH_2)_{1-3}CO_2H$, alkyl, alkoxy, alkenyl, aryl, heteroaryl, arylalkyl, and heteroarylalkyl.

In another example the compound is according to paragraph [0026], wherein Z is —$C(R^{15})$= or —$C(H)$=; $L^4$ is —O—; and p is at least one.

In another example the compound is according to paragraph [0027], wherein Ar is selected from the group consisting of phenyl, biphenyl, napthyl, tetrahydronaphthalene, chromen-2-one, dibenzofuran, pyryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl, each optionally substituted.

In another example the compound is according to paragraph [0028], wherein Ar is phenyl, optionally substituted, with at least one halogen.

In another example the compound is according to paragraph [0029], wherein p is at least two.

In another example the compound is according to paragraph [0030], wherein -$L^1$-$R^1$ is —$C(=O)OR^{14}$ or —$(CH_2)_2OR^{14}$.

In another example the compound is according to paragraph [0031], having the structure:

In another example the compound is according to paragraph [0026], wherein Z is —N=; and $L^4$ is —O—.

In another example the compound is according to paragraph [0033], wherein Ar is selected from the group consisting of phenyl, biphenyl, napthyl, tetrahydronaphthalene, chromen-2-one, dibenzofuran, pyryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl, each optionally substituted.

In another example the compound is according to paragraph [0034], wherein Ar is optionally substituted tetrahydronaphthalene.

In another example the compound is according to paragraph [0035], wherein -$L^1$-$R^1$ is —$C(=O)OR^{14}$ or —$(CH_2)_{2-3}OR^{14}$.

In another example the compound is according to paragraph [0036], wherein p is zero.

In another example the compound is according to paragraph [0037], having the structure:

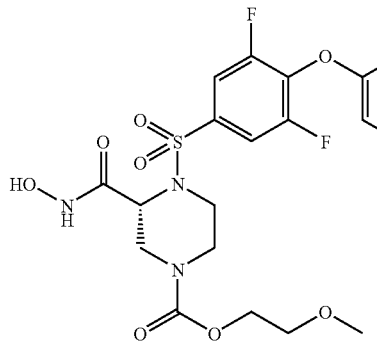

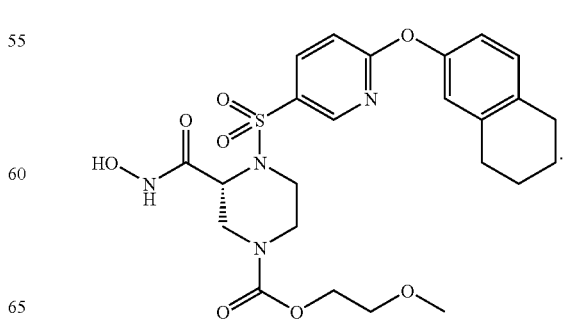

In another example the compound is according to paragraph [0026], wherein Z is —N═; and $L^4$ is nothing.

In another example the compound is according to paragraph [0039], wherein Ar is selected from the group consisting of phenyl, biphenyl, napthyl, tetrahydronaphthalene, chromen-2-one, dibenzofuran, pyryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl, each optionally substituted.

In another example the compound is according to paragraph [0040], wherein p is zero.

In another example the compound is according to paragraph [0041], wherein Ar is optionally substituted phenyl.

In another example the compound is according to paragraph [0042], wherein -$L^1$-$R^1$ is —C(═O)$OR^{14}$ or —$(CH_2)_{2-3}OR^{14}$.

In another example the compound is according to paragraph [0043], having the structure:

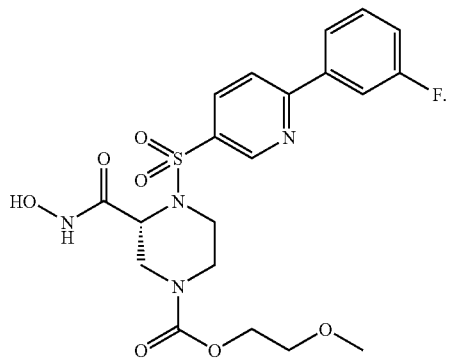

In another example the compound is according to paragraph [0026], of formula V,

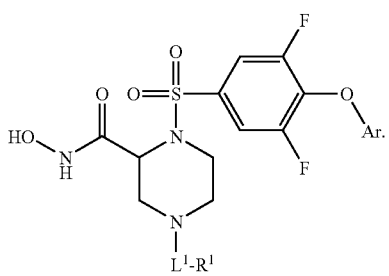

V

In another example the compound is according to paragraph [0045], wherein Ar is selected from the group consisting of phenyl, biphenyl, napthyl, tetrahydronaphthalene, chromen-2-one, dibenzofuran, pyryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl, each optionally substituted.

In another example the compound is according to paragraph [0046], wherein Ar is phenyl, optionally substituted, with at least one halogen.

In another example the compound is according to paragraph [0046], wherein Ar is selected from,

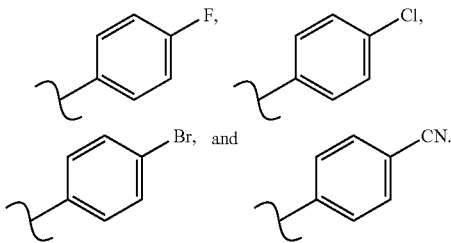

In another example the compound is according to paragraph [0047], wherein the absolute stereochemistry is according to formula VI,

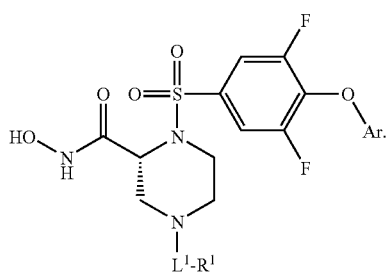

VI

In another example the compound is according to paragraph [0049], wherein -$L^1$-$R^1$ is —C(═O)$OR^{14}$ or —$(CH_2)_{2-3}OR^{14}$.

In another example the compound is according to paragraph [0050], having the structure:

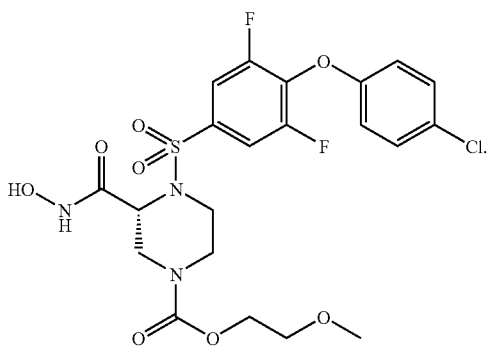

In another example, the invention comprises a pharmaceutical composition comprising a compound as described in any of paragraphs [0013]-[0051] and a pharmaceutically acceptable carrier.

In another example, the invention comprises a method of making a bis-aryl ether sulfonyl halide according to formula VII:

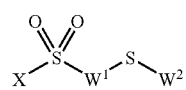

VII wherein X is a halide; and $W^1$ and $W^2$ are each independently an optionally substituted aryl, the method comprising: (a) combining a metal-aryloxide salt of a corresponding hydroxide-substituted aryl compound with a fluoro-substituted nitro aryl compound to make a bis-aryl ether nitro-aromatic compound; (b) reducing a nitro group of the bis-aryl ether nitro-aromatic compound to produce a corresponding aniline derivative; and (c) converting the corresponding aniline derivative to the bis-aryl ether sulfonyl halide.

In one example, the method is according to paragraph [0053], wherein the metal-aryloxide salt is combined with the fluoro-substituted nitro aryl in an organic solvent.

In another example, the method is according to paragraph [0054], wherein the organic solvent comprises at least one of DMF and acetonitrile.

In another example, the method is according to paragraph [0055], wherein the metal-aryloxide salt comprises at least one of a cesium salt and a potassium salt.

In another example, the method is according to paragraph [0056], wherein the corresponding aniline derivative is converted to the bis-aryl ether sulfonyl halide via a diazonium intermediate of said corresponding aniline derivative.

In another example, the method is according to paragraph [0057], wherein the fluoro-substituted nitro aryl compound is 3,4,5-trifluornitrobenzene.

In another example, the method is according to paragraph [0058], wherein the metal-aryloxide salt is a cesium salt.

In another example, the method is according to paragraph [0059], wherein the corresponding hydroxide-substituted aryl compound is 4-chlorophenol.

In another example, the method is according to paragraph [0060], wherein the bis-aryl ether sulfonyl halide is 4-(4-chlorophenoxy)-3,5-difluorophenylsulfonyl chloride.

In another aspect, the invention comprises a sulfonyl halide according to formula VIII:

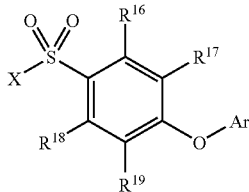

VIII wherein X is halogen; $R^{16}$, $R^{17}$, $R^{18}$, and $R^{19}$, are each independently either —H or —F; and Ar is aryl or heteroaryl, each optionally substituted.

In another example, the sulfonyl halide is according to paragraph [0062], wherein $R^{16}$ and $R^{18}$ are each —H; and $R^{17}$ and $R^{19}$ are each —F.

In another example the sulfonyl halide is according to paragraph [0063], wherein Ar is selected from the group consisting of phenyl, biphenyl, napthyl, tetrahydronaphthalene, chromen-2-one, dibenzofuran, pyryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl, each optionally substituted.

In another example the sulfonyl halide is according to paragraph [0064], wherein Ar is phenyl, optionally substituted, with at least one halogen.

In another example the sulfonyl halide is according to paragraph [0065], of formula IX:

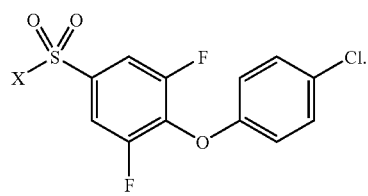

IX

In another example, the sulfonyl halide is according to paragraph [0066], wherein X is —Cl.

Yet another example of the invention is a method of treating cancer, arthritis, and diseases related to angiogenesis comprising administering to a mammal in need of such treatment a therapeutically effective amount of a pharmaceutical composition according to paragraph [0052].

Still yet another example of the invention is a method of modulating the activity of Adam-10 comprising administering to a mammal in need of such treatment a therapeutically effective amount of a pharmaceutical composition according to paragraph [0052].

DEFINITIONS

The following paragraphs provide definitions of the various chemical moieties that make up the compounds of the invention and are intended to apply uniformly throughout the specification and claims unless expressly stated otherwise.

The term alkyl refers inclusively to a univalent $C_1$ to $C_H$ (unless explicitly stated otherwise) saturated straight, branched, cyclic, and combinations thereof alkane moiety and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. In certain instances, specific cycloalkyls are defined (e.g. $C_3$-$C_8$ cycloalkyl) to differentiate them from generically described alkyls (that, again, are intended to construe inclusion of cycloalkyls). Thus "alkyl" includes, e.g., $C_3$-$C_8$ cycloalkyl. The term "alkyl" also includes, e.g., $C_3$-$C_8$ cycloalkyl $C_1$-$C_6$ alkyl, which is a $C_1$-$C_6$ alkyl having a $C_3$-$C_8$ cycloalkyl terminus. Alkyl's can be optionally substituted with any appropriate group, including but not limited to one or more moieties selected from halo, hydroxyl, amino, arylalkyl, heteroarylalkyl, alkylamino, arylamino, alkoxy, aryloxy, nitro, cyano, sulfonic acid, sulfate, phosphonic acid, phosphate, or phosphonate, either unprotected, or protected as necessary, as known to those skilled in the art or as taught, for example, in Greene, et al., "Protective Groups in Organic Synthesis," John Wiley and Sons, Second Edition, 1991.

The term alkoxy refers to the group —O-(substituted alkyl), the substitution on the alkyl group generally containing more than only carbon (as defined by alkoxy). One exemplary substituted alkoxy group is "polyalkoxy" or —O—(optionally substituted alkylene)-(optionally substituted alkoxy), and includes groups such as —OCH$_2$CH$_2$OCH$_3$, and glycol ethers such as polyethyleneglycol and —O(CH$_2$CH$_2$O)$_x$CH$_3$, where x is an integer of between about 2 and about 20, in another example, between about 2 and about 10, and in a further example between about 2 and about 5. Another exemplary substituted alkoxy group is hydroxyalkoxy or —OCH$_2$(CH$_2$)$_y$OH, where y is for example an integer of between about 1 and about 10, in another example y is an integer of between about 1 and about 4.

The term alkenyl refers to a univalent $C_2$-$C_6$ straight, branched, or in the case of $C_{5-8}$, cyclic hydrocarbon with at least one double bond.

The term aryl refers to a univalent phenyl, biphenyl, napthyl, and the like. The aryl group can be optionally substituted with any suitable group, including but not limited to one or more moieties selected from halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991). As well, substitution on an aryl can include fused rings such as in tetrahydronaphthalene, chromen-2-one, dibenzofuran, and the like. In such cases, e.g. tetrahydronaphthalene, the aryl portion of the tetrahydronaphthalene is attached to the portion of a molecule described as having an aryl group.

The term heteroatom means O, S, P, or N.

The term heterocycle refers to a cyclic alkyl, alkenyl, or aryl moiety as defined above wherein one or more ring carbon atoms is replaced with a heteroatom.

The term heteroaryl specifically refers to an aryl that includes at least one of sulfur, oxygen, and nitrogen in the aromatic ring. Non-limiting examples are pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl.

The term halo refers to chloro, fluoro, iodo, or bromo.

As used herein, the term pharmaceutically acceptable salts or complexes refers to salts or complexes that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenyl-acetate).

The term pharmaceutically active derivative refers to any compound that upon administration to the recipient, is capable of providing directly or indirectly, the compounds disclosed herein.

In some examples, as will be appreciated by those skilled in the art, two adjacent carbon containing groups on an aromatic system may be fused together to form a ring structure. The fused ring structure may contain heteroatoms and may be substituted with one or more substitution groups "R". It should additionally be noted that for cycloalkyl (i.e. saturated ring structures), each positional carbon may contain two substitution groups, e.g. R and R'.

Some of the compounds of the invention may have imino, amino, oxo or hydroxy substituents off aromatic heterocyclic ring systems. For purposes of this disclosure, it is understood that such imino, amino, oxo or hydroxy substituents may exist in their corresponding tautomeric form, i.e., amino, imino, hydroxy or oxo, respectively.

Compounds of the invention are generally named using ACD/Name (available from Advanced Chemistry Development, Inc. of Toronto, Canada). This software derives names from chemical structures according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. When desired, the R- and S-isomers may be resolved by methods known to one skilled in the art, for example by: formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Optional" or "optionally" means that the subsequently described event or circumstance may or may not occur, and that the description includes instances where said event or circumstance occurs and instances in which it does not. It will be understood by one skilled in the art with respect to any group containing one or more substituents that such groups are not intended to introduce any substitution or substitution patterns that are sterically impractical and/or synthetically non-feasible. "Optionally substituted" refers to all subsequent modifiers in a term, for example in the term "optionally substituted $C_{1-8}$alkylaryl," optional substitution may occur on both the "$C_{1-8}$alkyl" portion and the "aryl" portion of the molecule; and for example, optionally substituted alkyl includes optionally substituted cycloalkyl groups, which in turn are defined as including optionally substituted alkyl groups, potentially ad infinitum.

"Substituted" alkyl, aryl, and heterocyclyl, for example, refer respectively to alkyl, aryl, and heterocyclyl, wherein one or more (for example up to about 5, in another example, up to about 3) hydrogen atoms are replaced by a substituent independently selected from, but not limited to: optionally substituted alkyl (e.g., fluoroalkyl), optionally substituted alkoxy, alkylenedioxy (e.g. methylenedioxy), optionally substituted amino (e.g., alkylamino and dialkylamino), optionally substituted amidino, optionally substituted aryl (e.g., phenyl), optionally substituted arylalkyl (e.g., benzyl), optionally substituted aryloxy (e.g., phenoxy), optionally substituted arylalkyloxy (e.g., benzyloxy), carboxy (—COOH), carboalkoxy (i.e., acyloxy or —OOCR), carboxyalkyl (i.e., esters or —COOR), carboxamido, aminocarbonyl, benzyloxycarbonylamino (CBZ-amino), cyano, carbonyl, halogen, hydroxy, optionally substituted heterocyclylalkyl, optionally substituted heterocyclyl, nitro, sulfanyl, sulfinyl, sulfonyl, and thio.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about 1 and about 6 carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about 1 and about 6 carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

"Metabolite" refers to the break-down or end product of a compound or its salt produced by metabolism or biotransformation in the animal or human body; e.g., biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be synthesized such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

EXPERIMENTAL SECTION

The compounds of the invention can be made in accordance with the following general description and following the teachings provided in the Example Section, below, and methods routine to those of ordinary skill in the art. The examples are merely illustrative and are not intended to be limiting.

N-Hydroxy-1,4-disubstituted piperazine-2-carboxamides of the present invention can be synthesized using the methods described below. Method A begins with the reaction of piperazine-2-(R)-carboxylic acid dihydrochloride (1), for example, with di-tert-butyl dicarbonate to yield the bis-Boc protected intermediate 2, which is esterified, for example, with methyl iodide in the presence of cesium carbonate to form methyl ester 3. The Boc groups are then removed from 3 to yield piperazine dihydrochloride intermediate 4.

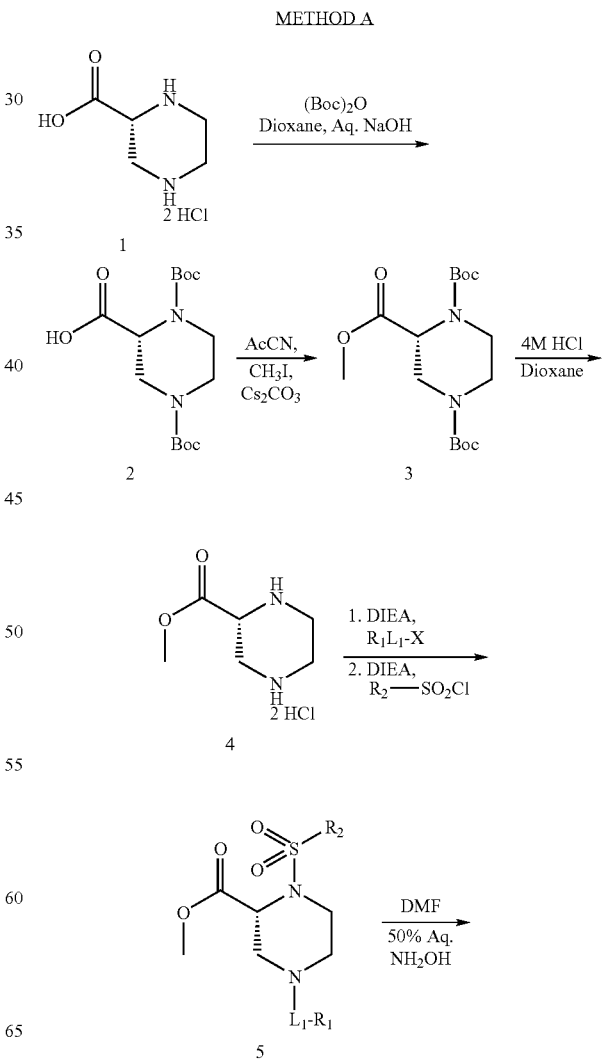

METHOD A

-continued

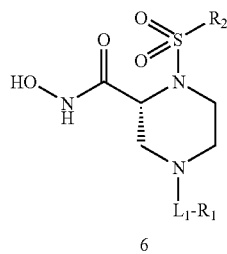

6

In one pot, the N4 nitrogen of 4 is selectively acylated, carbamylated, sulfonylated, alkylated, and the like, followed by sulfonylation of the N1 nitrogen to form the disubstituted piperazine 5. The methyl ester group of 5 is then converted to the hydroxamate in a mixture of DMF and 50% aqueous hydroxylamine, for example, to give the corresponding N-hydroxy-1,4-disubstituted piperazine-2-(R)-carboxamide 6, in accordance with formula I.

Method B begins with the sulfonylation of the N1 nitrogen of mono-Boc protected piperazine-2-(R)-carboxylic acid 7, for example, through the use of trimethylsilyl chloride and an appropriate sulfonyl chloride (see synthesis below) to form intermediate 8. Intermediate 8 is then esterifed with TMS-diazomethane to form methyl ester 9, followed by deprotection of the Boc group with TFA to form the TFA salt of 10. Alternatively, compound 8 can be simultaneously esterified and Boc-deprotected using HCl in methanol to form the HCl salt of 10. The N4 nitrogen of 10 is acylated, carbamylated, sulfonylated, alkylated, etc. to form methyl ester 5, which is converted to the hydroxamate 6 (see structure in Method A description) using a mixture of DMF and 50% aqueous hydroxylamine as described above or, alternatively, by treatment with hydroxylamine under basic conditions (KOH in MeOH).

nitrogen of 1 is selectively Boc-protected, followed by the addition of triethylamine and the appropriate sulfonyl chloride to sulfonylate the N1 nitrogen to form 8. From intermediate 8, the desired hydroxamates 6 are formed as described in Method B.

METHOD C

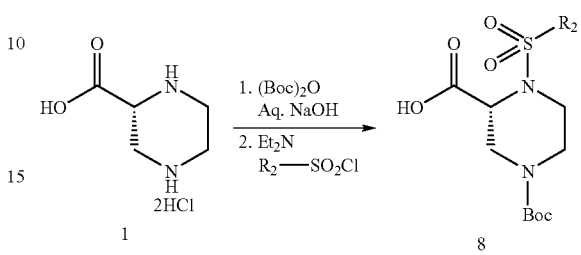

EXAMPLE SECTION

Example 1

N-Hydroxy-1-[4-(4-fluorophenoxy)-phenyl)]sulfonyl-4-(4-morpholinyl-carbonyl)piperazine-2-(R)-carboxamide (Method A)

Step 1—Formation of 1,4-di-tert-butoxycarbonylpiperazine-2-(R)-carboxylic acid. piperazine-2-(R)-carboxylic acid dihydrochloride (16.6 g, 82 mmol) and dioxane (120 ml) were combined and cooled in an icebath. 5N NaOH (60 ml, 300 mmol) was added, followed by (Boc)$_2$O (41.8 g, 191 mmol). The reaction mixture was allowed to warm to room temperature with stirring over several hours, then concentrated in vacuo. The resulting aqueous mixture was washed

METHOD B

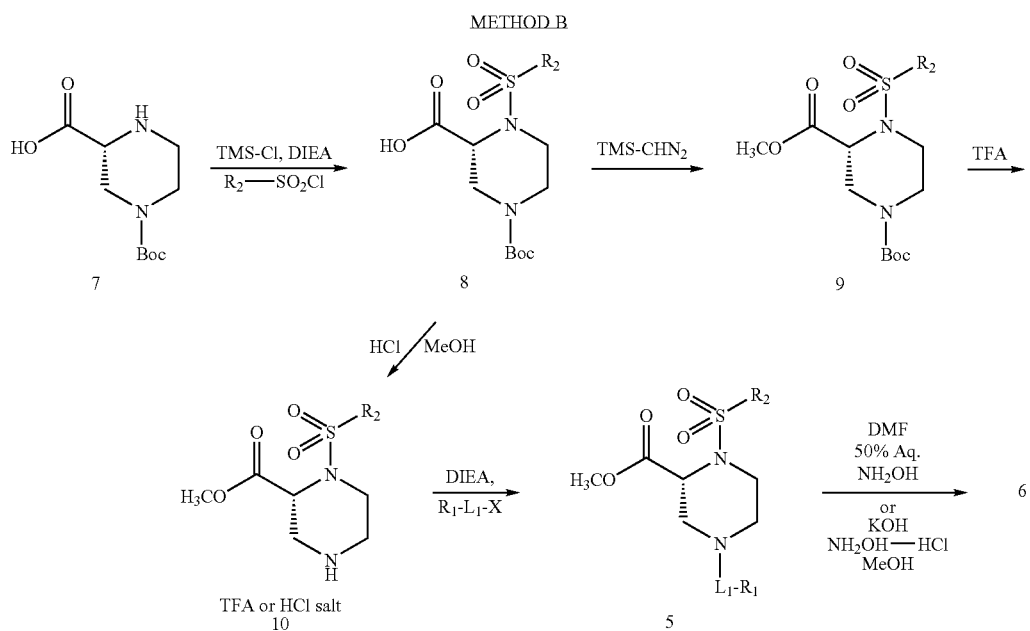

Method C begins with the one pot synthesis of the disubstituted piperazine-2-(R)-carboxylic acid 8 from the dihydrochloride 1. First, under Schotten-Baumann conditions, the N4 with Et$_2$O (3×), cooled in an icebath, acidified to pH 2-3 with concentrated HCl and extracted with EtOAc (3×). Combined EtOAc extractions were washed with water (1×), saturated NaCl (1×), dried (Na₂SO₄), and concentrated in vacuo to give 1,4-di-tert-butoxycarbonylpiperazine-2-(R)-carboxylic acid as a white solid (27.0 g, 100%). LC/MS Calcd for [M–H]⁻ 329.2. found 329.2.

Step 2—Formation of methyl 1,4-di-tert-butoxycarbonyl piperazine-2-(R)-carboxylate 1,4-Di-tert-butoxycarbonylpiperazine-2-(R)-carboxylic acid (70 g, 212 mmol) was dissolved in acetonitrile (1.3 L). Cs₂CO₃ (110 g, 340 mmol) was added and the mixture stirred for 30 minutes at room temperature before the addition of methyl iodide (28 ml, 450 mmol). The reaction mixture was stirred at room temperature overnight, solids were filtered and the filtrate concentrated in vacuo. The resulting oil was dissolved in EtOAc and any insoluble material filtered. The filtrate was concentrated in vacuo to give methyl 1,4-di-tert-butoxycarbonylpiperazine-2-(R)-carboxylate (69 g, 95%). LC/MS Calcd for [M+H]⁺ 345.2. found 145.1 (–Boc×2).

Step 3—Formation of methyl piperazine-2-(R)-carboxylate dihydrochloride. Methyl 1,4-di-tert-butoxycarbonylpiperazine-2-(R)-carboxylate (2.9 g, 8.5 mmol) was dissolved in 4M HCl in dioxane (30 ml) and stirred at room temperature for 30-60 minutes, forming a thick white precipitate. The reaction mixture was concentrated in vacuo and the resulting white solid dried under high vacuum to give methyl piperazine-2-(R)-carboxylate dihydrochloride (1.9 g, 100%). LC/MS Calcd for [M+H]⁺ 145.1. found 145.1.

Step 4—Formation of methyl 1-[4-(4-fluoro-phenoxy)phenyl)]sulfonyl-4-(4-morpholinylcarbonyl)pipera-zine-2-(R)-carboxylate Methyl piperazine-2-(R)-carboxylate dihydrochloride (676 mgs, 3.1 mmol) was dissolved in CH₂Cl₂ (7 mls) and DIEA (2.1 mls, 12.4 mmol) and cooled in an icebath. Morpholinecarbonyl chloride (450 mgs, 3.0 mmol) dissolved in methylene chloride (2.5 mls) was added dropwise with stirring. After addition was complete, the reaction mixture was allowed to warm to room temperature and stirred for an additional 2-3 hrs. Additional DIEA (0.6 mls, 3.4 mmol) was added, followed by 4-(4-fluorophenoxy)phenylsulfonyl chloride (904 mg, 3.1 mmol) and the reaction mixture stirred at room temperature overnight. The reaction mixture was concentrated in vacuo and the resulting residue redissolved in EtOAc and washed with water (1×), 1.0N HCl (2×), dried (Na₂SO₄), concentrated in vacuo and purified by flash chromatography (3:1 EtOAc:hexanes) to give methyl 1-[4-(4-fluorophenoxy)phenyl)]sulfonyl-4-(4-morpholinylcarbonyl)piperazine-2-(R)-carboxylate (1.11 g, 70%). LC/MS Calcd for [M+H]⁺ 508.1. found 508.1.

Step 5—Formation of N-hydroxy-1-[4-(4-fluorophenoxy)phenyl)]sulfonyl-4-(4-morpholinylcarbonyl)piperazine-2-(R)-carbox-amide Methyl 1-[4-(4-fluorophenoxy)phenyl)]sulfonyl-4-(4-morpholinylcarbonyl)piperazine-2-(R)-carboxylate (1.11 g, 2.2 mmol) was dissolved in DMF (17 mls) to which was added 50% aqueous NH₂OH (20 mls) and the reaction mixture stirred at room temperature overnight. The reaction mixture was poured into cold 1.0N HCl (100-120 mls) and extracted with EtOAc (4×). The combined EtOAc extractions were washed with 10% aqueous LiCl (4×), saturated NaCl (1×), dried (Na₂SO₄), and concentrated in vacuo. The crude product was purified by flash chromatography (EtOAc) and the resulting pure oil was dissolved in 1:1 acetonitrile:water and lyophilized to give N-hydroxy-1-[4-(4-fluorophenoxy)phenyl)]sulfonyl-4-(4-morpholinylcarbonyl)piperazine-2-(R)-carboxamide as a white solid (659 mg, 59%). LC/MS Calcd for [M+H]⁺ 509.1. found 509.1. ¹HNMR (400 MHz, CD₃OD): δ 7.69 (d, 2H, J=9.2 Hz), 7.04 (m, 4H), 6.95 (d, 2H, J=9.2 Hz), 4.30 (m, 1H), 3.76 (m, 1H), 3.50 (m, 7H), 3.10 (m, 4H), 2.90 (dd, 1H, J=13.2, 4.4 Hz), 2.72 (m, 1H).

Example 2

N-Hydroxy-1-[4-(4-fluorophenoxy)-3,5-difluorophenyl)]sulfonyl-4-(ethoxycarbonyl)piperazine-2-(R)-carboxamide (Method B)

Step 1—Formation of 1-[4-(4-fluorophenoxy)-3,5-difluoro-phenyl)]sulfonyl-4-boc-piperazine-2-(R)-carboxylic acid 4-Boc-piperazine-2-(R)-carboxylic acid (933 mg, 4.05 mmol), CH₂Cl₂ (12 ml), DMF (6 ml), and DIEA (2.5 ml, 14.3 mmol) were combined under N₂. TMS-Cl (810 µl, 6.38 mmol) was added slowly and the mixture stirred at room temperature for approximately 2 hrs. 4-(4-fluorophenoxy)-3,5-difluorophenyl)]sulfonyl chloride (1.43 g, 4.43 mmol) dissolved in a minimum of CH₂Cl₂ was added and the mixture stirred at room temperature for another 2 hrs. The reaction mixture was diluted with EtOAc and washed with 0.5N HCl (3×), sat'd NaCl (1×), dried (Na₂SO₄), and concentrated in vacuo. The resulting crude oil was purified by flash chromatography (6:4 hexanes:EtOAc+1% AcOH) to give the desired product (1.37 g, 65%). LC/MS Calcd for [M+H]⁺ 517.1. found 417.0 (–Boc).

Step 2—Formation of methyl 1-[4-(4-fluorophenoxy)-3,5-difluorophenyl)]sulfonyl-4-boc-piperazine-2-(R)-carboxylate. 1-[4-(4-fluorophenoxy)-3,5-difluorophenyl)]sulfonyl-4-boc-piperazine-2-(R)-carboxylic acid (1.37 g, 2.65 mmol) was dissolved in CH₂Cl₂ (40 ml) and MeOH (10 ml). A mixture of 2M TMS-CHN₂ in hexanes (2.5 ml, 5 mmol) and CH₂Cl₂ (10 ml) was added dropwise with stirring and the reaction followed by TLC. Upon completion of the reaction, AcOH (1.0 ml) was added dropwise with stirring. The reaction mixture was further diluted with CH₂Cl₂ and washed with water (1×), saturated NaHCO₃ (2×), saturated NaCl (1×), dried (MgSO₄), and concentrated in vacuo. The crude oil was purified by flash chromatography (3:1 hexanes:EtOAc) to give the desired product (1.10 g, 78%). LC/MS Calcd for [M+H]⁺ 531.1. found 431.0 (–Boc).

Step 3—Formation of methyl 1-[4-(4-fluorophenoxy)-3,5-difluorophenyl)]sulfonyl-piperazine-2-(R)-carboxylate TFA salt. Methyl 1-[4-(4-fluorophenoxy)-3,5-difluorophenyl)]sulfonyl-4-boc-piperazine-2-(R)-carboxylate (1.10 g, 2.07 mmol) was dissolved in a minimum of CH₂Cl₂ to which was added neat TFA (10 ml). The mixture was stirred at room temperature for approximately 30 min, concentrated in vacuo, further dried for several hours under high vacuum and used without further purification. LC/MS Calcd for [M+H]⁺ 431.1. found 431.0.

Step 4—Formation of methyl 1-[4-(4-fluorophenoxy)-3,5-difluorophenyl)]sulfonyl-4-(ethoxycarbonyl) piperazine-2-(R)carboxylate. To a mixture of methyl 1-[4-(4-fluorophenoxy)-3,5-difluorophenyl)]sulfonyl-piperazine-2-(R)-carboxylate TFA salt (344 mg, 0.63 mmol), CH₂Cl₂ (10 ml), and DIEA (250 µl, 1.43 mmol) under N₂ was added ethyl chloroformate (65 µl, 0.68 mmol). The mixture was stirred under N₂ at room temperature for 1.5 hrs, then washed with 1.0N HCl (2×), saturated NaCl (1×), dried (Na₂SO₄), and concentrated in vacuo. The crude residue was purified by flash chromatography (3:1 hexanes:EtOAc) to give the desired product (218 mgs, 69%). LC/MS Calcd for [M+H]⁺ 503.1. found 503.0.

Step 5—Formation of N-hydroxy-1-[4-(4-fluorophenoxy)-3,5-difluorophenyl)]sulfonyl-4-(ethoxycarbonyl)piperazine-2-(R)-carboxamide. A 1.7M solution of NH₂OH in MeOH was prepared by mixing a solution of KOH (2.80 g, 50.0 mmol) in MeOH (7.0 ml) with a hot solution of NH$_2$OH HCl salt (2.40 g, 34.5 mmol) in MeOH (12.0 ml) and filtering the resulting solids after cooling to room temperature. Methyl 1-[4-(4-fluorophenoxy)-3,5-difluorophenyl)]-sulfonyl-4-(ethoxycarbonyl)piperazine-2-(R)-carboxylate (218 mg, 0.43 mmol) was dissolved in the 1.7M NH$_2$OH in MeOH solution (4.0 ml) and stirred at room temperature for 30-45 minutes. The reaction mixture was then diluted with 1.0N HCl and extracted with EtOAc (3×). Combined EtOAc extractions were washed with saturated NaCl (1×), dried (Na$_2$SO$_4$), and concentrated in vacuo. The resulting crude residue was purified by flash chromatography (1:1 EtOAc: hexanes) to give a colorless film which was lyophilized from 1:1 AcCN:H$_2$O to give the desired product as a white solid (136 mg, 62%). LC/MS Calcd for [M+H]$^+$ 504.1. found 504.0. $^1$HNMR (400 MHz, CD$_3$OD): δ 7.58 (m, 2H), 7.03 (m, 4H), 4.27 (m, 2H), 4.07 (m, 3H), 3.75 (m, 2H), 3.30 (m, 1H), 3.06 (m, 1H), 1.22 (m, 3H).

Example 3

N-Hydroxy-1-[4-(4-cyanophenoxy)-3-fluorophenyl)]sulfonyl-4-(2-methoxy-1-ethoxycarbonyl)piperazine-2-(R)-carboxamide (Method C)

Step 1—Formation of 1-[4-(4-cyanophenoxy)-3-fluorophenyl)]sulfonyl-4-boc-piperazine-2-(R)-carboxylic acid. Piperazine-2-(R)-carboxylic acid dihydrochloride (1.25 g, 6.1 mmol), dioxane (15 mls) and water (6.0 mls) were combined and cooled in an icebath. 9N NaOH (2.0 mls, 18 mmol) was added slowly with stirring, followed by (Boc)$_2$O (1.35 g, 6.2 mmol). The reaction mixture was allowed to warm to room temperature and stirred for an additional 3-4 hrs. Et$_3$N (1.8 mls, 13 mmol) was added, followed by 4-cyanophenoxy-3-fluorophenylsulfonyl chloride (2.00 g, 6.4 mmol). The reaction mixture is stirred at room temperature for 1-2 hrs, then concentrated in vacuo. The resulting residue was partitioned between 1.0N HCl and EtOAc. Phases were separated and the aqueous phase was further extracted with EtOAc (2×). Combined EtOAc extractions were washed with 1.0N HCl (1×), saturated NaCl (1×), dried (MgSO$_4$), and concentrated in vacuo. The resulting residue is purified by flash chromatography (7:3 hexanes:EtOAc+1% AcOH) to give the desired product (1.1 g, 35%). LC/MS Calcd for [M–H]$^-$ 504.1. found 504.3.

Step 2. Methyl 1-[4-(4-cyanophenoxy)-3-fluorophenyl)]sulfonyl-4-boc-piperazine-2-(R)-carboxylate was made in the same manner as Example 2, step 2, except purification by flash chromatography was unnecessary. 1.10 g recovered (97%). LC/MS Calcd for [M+H]$^+$ 520.1. found 420.1 (–Boc).

Step 3. Methyl 1-[4-(4-cyanophenoxy)-3-fluorophenyl)]sulfonyl-piperazine-2-(R)-carboxylate TFA salt was made in the same manner as Example 2, step 3. LC/MS Calcd for [M+H]$^+$ 420.1. found 420.2.

Step 4. Methyl 1-[4-(4-cyanophenoxy)-3-fluorophenyl)]sulfonyl-4-(2-methoxy-1-ethoxycarbonyl) piperazine-2-(R) carboxylate was made in the same manner as Example 2, step 4. 438 mgs recovered (83%). LC/MS Calcd for [M+H]$^+$ 522.1. found 522.2.

Step 5. N-Hydroxy-1-[4-(4-cyanophenoxy)-3-fluorophenyl)]sulfonyl-4-(2-methoxy-1-ethoxycarbonyl)piperazine-2-(R)-carboxamide was made in the same manner as Example 2, step 5. 46 mg recovered (10%). LC/MS Calcd for [M–H]$^-$ 521.1. found 521.2. $^1$HNMR (400 MHz, CD$_3$OD): δ 7.73 (m, 3H), 7.65 (m, 1H), 7.34 (m, 1H), 7.19 (d, 2H, J=8.4 Hz), 4.29 (m, 2H), 4.14 (m, 3H), 3.74 (m, 2H), 3.55 (m, 2H), 3.33 (s, 3H), 3.25 (m, 1H), 3.04 (m, 1H).

Example 4

Synthesis of Sulfonyl Chloride Intermediates

Example 4a 4-(4-fluorophenoxy)-3,5-difluorophenylsulfonyl chloride

Step 1. A mixture of 3,4,5-trifluoronitrobenzene (20.0 g, 113 mmol, commercially available from AsymChem of Durham, N.C.), dry DMF (100 ml), 4-fluorophenol (13.9 g, 124 mmol), and Cs$_2$CO$_3$ (56 g, 172 mmol) was stirred under N$_2$ at 60-70° C. for 1-2 hrs. After cooling to room temperature, the reaction mixture was partitioned between H$_2$O and EtOAc. The phases were separated and the aqueous phase was further extracted with EtOAc (2×). The EtOAc extractions were washed with sat'd NaCl (1×), dried over Na$_2$SO$_4$, and concentrated in vacuo to give 4-(4-fluorophenoxy)-3,5-difluoronitrobenzene (32.0 g, 105%) which was used in the next step without further purification. $^1$H NMR (DMSO-d$_6$): δ7.15 (m, 2H), 7.22 (m, 2H), 8.31 (d, 2H, J=7.6 Hz).

Step 2. A mixture of 4-(4-fluorophenoxy)-3,5-difluoronitrobenzene (30.4 g, 113 mmol), EtOAc (300 ml), 10% Pd/C (2.6 g) was stirred under an atmosphere of H$_2$ at room temperature and pressure for approximately 6 hrs. The reaction mixture was filtered through Celite and concentrated in vacuo to give 4-(4-fluorophenoxy)-3,5-difluoroaniline (26.5 g, 98%) which was used in the next step without further purification. $^1$H NMR (CDCl$_3$): δ 3.82 (s, 2H), 6.26 (d, 2H, J=8.4 Hz), 6.88 (m, 2H), 6.93 (m, 2H).

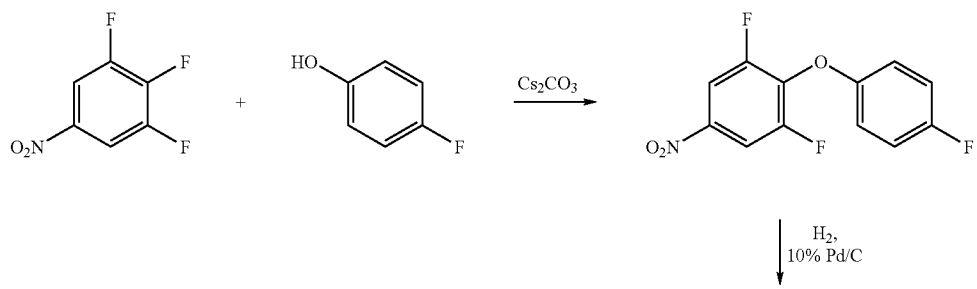

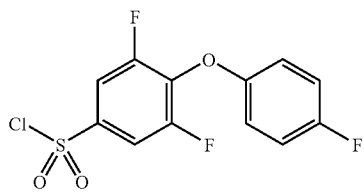
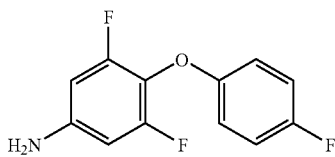

Step 3. A solution of NaNO₂ (8.4 g, 122 mmol) in H₂O (20 ml) was added dropwise to a mixture of 4-(4-fluorophenoxy)-3,5-difluoroaniline (26.5 g, 111 mmol), AcOH (160 ml), and conc. HCl (160 ml) cooled in an ice/NaCl/H₂O bath. After addition was complete, the mixture was stirred an additional 20-30 minutes before a mixture of SO₂ (74 g, 1.15 mol) in AcOH (140 ml) and CuCl₂-2H₂O (11.1 g, 65 mmol) in H₂O (16 ml) was added. The reaction mixture was removed from the ice bath and stirred at room temperature for 1-2 hrs. The reaction mixture was poured into ice water and extracted with CH₂Cl₂ (3×). The combined CH₂Cl₂ extractions were washed with sat'd NaCl (1×), dried over Na₂SO₄, and concentrated in vacuo. The resulting crude oil was purified by flash chromatography (9:1 hexanes:EtOAC) to give 4-(4-fluorophenoxy)-3,5-difluorophenyl sulfonyl chloride (29.8 g, 83%). ¹H NMR (CDCl₃): δ 6.94 (m, 2H), 7.10 (m, 2H), 7.71 (d, 2H, J=6.4 Hz).

Example 4b

4-(4-Chlorophenoxy)-3,5-difluorophenylsulfonyl chloride

Step 1. A mixture of 3,4,5-trifluoronitrobenzene (6.6 g, 37 mmol), dry DMF (30 ml), 4-chlorophenol (5.26 g, 41 mmol), and Cs₂CO₃ (18.8 g, 58 mmol) was stirred under N₂ at 60-70 C for 1-2 hrs. After cooling to room temperature, the reaction mixture was partitioned between H₂O and EtOAc. The phases were separated and the aqueous phase was further extracted with EtOAc (2×). The EtOAc extractions were washed with sat'd NaCl (1×), dried over Na₂SO₄, and concentrated in vacuo to give 4-(4-chlorophenoxy)-3,5-difluoronitrobenzene (11.3 g, 106%) which was used in the next step without further purification. ¹H NMR (CDCl₃): δ 6.90 (d, 2H, J=7.6 Hz), 7.28 (d, 2H, J=7.6 Hz), 7.94 (d, 2H, J=6.4 Hz). Note: K₂CO₃/acetonitrile can be used in lieu of Cs₂CO₃/DMF.

Step 2. A mixture of 4-(4-chlorophenoxy)-3,5-difluoronitrobenzene (10.6 g, 37 mmol), toluene (150 ml), H₂O (150 ml), iron powder (6.9 g, 124 mmol), and ammonium acetate (9.3 g, 120 mmol) was heated to reflux with stirring for 2-3 hrs. After cooling to room temperature, the reaction mixture was filtered through Celite with thorough washing with H₂O and EtOAc. The filtrate was transferred to a separatory funnel and the phases separated. The aqueous phase was further extracted with EtOAc (2×). The combined organic phases were washed with H₂O (1×), sat'd NaCl (1×), dried over Na₂SO₄, and concentrated in vacuo to give 4-(4-chlorophenoxy)-3,5-difluoroaniline (10.8 g, 113%) which was used in the next step without further purification. ¹H NMR (CDCl₃): δ 3.81 (s, 2H), 6.27 (d, 2H, J=9.2 Hz), 6.85 (d, 2H, J=9.2 Hz), 7.21 (d, 2H, J=9.2 Hz).

Step 3. A solution of NaNO₂ (2.8 g, 41 mmol) in H₂O (7.0 ml) was added dropwise to a mixture of 4-(4-chlorophenoxy)-3,5-difluoroaniline (9.5 g, 37 mmol), AcOH (50 ml), and conc. HCl (50 ml) cooled in an ice/NaCl/H₂O bath. After addition was complete, the mixture was stirred an additional 20-30 minutes before a mixture of SO₂ (25 g, 290 mmol) in AcOH (50 ml) and CuCl₂-2H₂O (3.8 g, 22 mmol) in H₂O (6.0 ml) was added. The reaction mixture was removed from the ice bath and stirred at room temperature for 1-2 hrs. The reaction mixture was poured into ice water and extracted with CH₂Cl₂ (3×). The combined CH₂Cl₂ extractions were washed with sat'd NaCl (1×), dried over Na₂SO₄, and concentrated in vacuo. The resulting crude oil was purified by flash chromatography (9:1 hexanes:EtOAC) to give 4-(4-chlorophenoxy)-3,5-difluorophenylsulfonyl chloride (11.0 g, 87%). ¹H NMR (CDCl₃): δ 6.92 (d, 2H, J=7.2 Hz), 7.30 (d, 2H, J=7.2 Hz), 7.72 (d, 2H, J=4.8 Hz).

Example 4c

3,4,5-trifluorobenzenesulfonyl chloride

To a 2000 mL round-bottomed flask was added 800 mL distilled H₂O and a stir bar. Upon stirring, the flask was

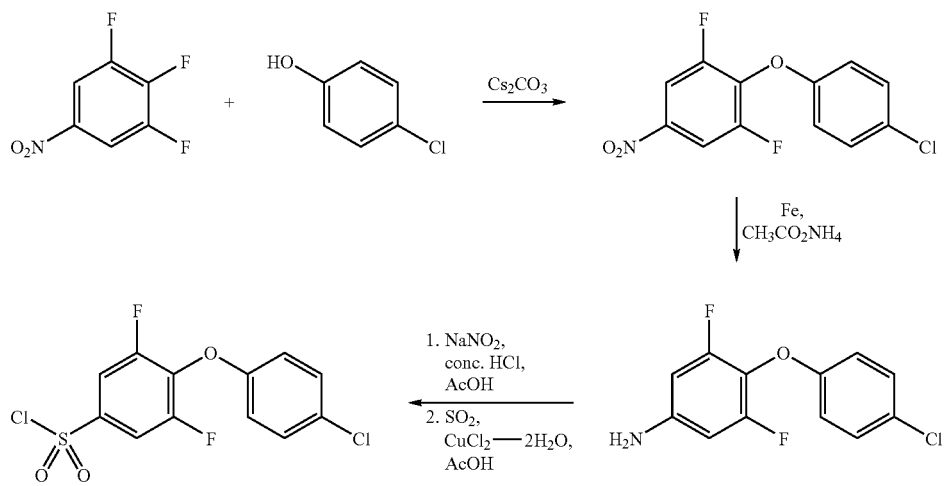

cooled to −10° C. in an ice-acetone bath. The flask was fitted with a 500 mL addition funnel and SOCl$_2$ (300 mL, 4.1 mol, 10 eq.) was added dropwise over a period of 1 h. After complete addition, the solution was stirred for 4 h while warming to room temperature.

Meanwhile, in a separate 500 mL recovery flask was added 3,4,5-trifluoroaniline (61 g, 0.41 mol, 1.0 eq.), conc. HCl (150 mL), and a stir bar. The resulting suspension was stirred vigorously and cooled to −10° C. The flask was fitted with a 250 mL addition funnel and a solution of NaNO$_2$ (34.3 g, 0.50 mol, 1.2 eq.) in H$_2$O (125 mL) was added to the suspension dropwise over a period of 10 min. The reaction mixture, now nearly homogeneous, is yellow-orange in color. The reaction mixture was stirred for an additional 30 min while carefully maintaining the temperature at −10° C.

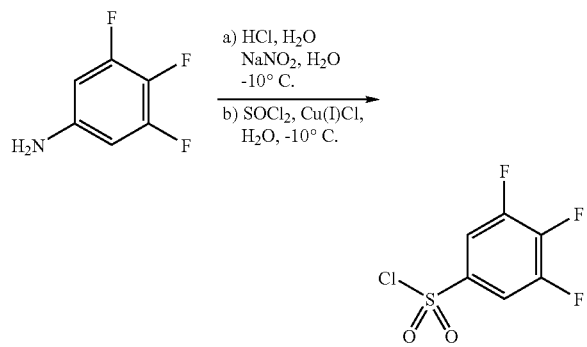

The flask containing the SOCl$_2$/H$_2$O solution is cooled again to −10° C. and a catalytic amount of Cu(I)Cl (~50 mg) was added. The solution turns dark green in color. The flask was fitted with a 500 mL addition funnel (previously chilled to 0° C.) and the 3,4,5-trifluorodiazobenzene solution was quickly transferred to the funnel. The solution was immediately added dropwise over a period of 3 min. After addition, the reaction mixture slowly turns darker green in color, but after stirring for 5 min becomes bright, lime green. The reaction was stirred for an additional hour while warming to room temperature. The reaction mixture was transferred to a separatory funnel and extracted with CH$_2$Cl$_2$ (3×200 mL). The organic phases are combined and dried over anhydrous Na$_2$SO$_4$, filtered, and concentrated to give a dark-bronze oil (79.5 g, 83%).

Example 5

Enzyme Assays mADAM-10 or hADAM-10 activity was measured as the ability to cleave a 10-residue peptide (DABCYL-Leu-Leu-Ala-Gln-Lys-*-Leu-Arg-Ser-Ser-Arg-EDANS). This peptide was based on the TNF-α cleavage site (Leu$^{62}$-Arg$^{71}$); however, we found that replacement of Ala$^{76}$-Val$^{77}$ with Lys-Leu resulted in a peptide with a 5-fold greater affinity for ADAM-10 than the native TNF-α peptide. Enzyme was diluted to a final active concentration of 5 nM in Buffer A (50 mM HEPES 8.0, 100 mM NaCl, 1 mM CaCl2 and 0.01% NP-40). Serial dilutions for compounds were performed ranging from 100 μM to 0.5 nM using a Beckman Biomek 2000 in polypropylene plates (Greiner). 20 μl of enzyme solution was added to 10 μl of compound in buffer A, and allowed to incubate for 15 min in 384 well black, Greiner, microtiter plates (#781076). 20 μl of substrate (12.5 μM in Buffer A) was then added, resulting in final reaction conditions of 2 nM ADAM-10, 5 μM substrate, and compound concentrations ranging from 20 uM to 0.1 nM. The reaction was incubated for 2 hr at RT, and fluorescence was measured at Ex355, Em460 on a Wallac Victor 2 fluorescence reader. For final analysis of potent inhibitors, a similar reaction was set up with a final active ADAM-10 concentration of 0.1 nM. This reaction was incubated for 16 hr at RT and fluorescence was read using identical conditions.

One aspect of the invention is, for example, piperazine-derived hydroximates according to formula I, which are selective ADAM-10 inhibitors. In one embodiment, such inhibitors comprise a bis-aryl ether substitution for —R$^2$ (—R$^{21}$-L$^2$-R$^{22}$, where R$^{21}$ is phenylene, L$^2$ is oxygen, and R$^{22}$ is phenyl), the proximal ring (R$^{21}$) of which is substituted particularly with one or more halogens, more particularly with one or more flourines, even more particularly with two or more flourines. For example, by combining such groups with appropriate substitution, -L$^1$-R$^1$ and —R$^{22}$, inhibitors that are selective for ADAM-10 are produced.

Table 5 below shows structure activity relationship data for selected compounds of the invention when tested in vitro with various metalloproteases. Inhibition is indicated as IC$_{50}$ with the following key: A=IC$_{50}$ less than 50 nM, B=IC$_{50}$ greater than 50 nM, but less than 1000 nM, C=IC$_{50}$ greater than 1000 nM, but less than 20,000 nM, and D=IC$_{50}$ greater than 20,000 nM. Blank cells indicate lack of data only. The abbreviations in Table 5 are defined as follows: TACE stands for TNF-alpha converting enzyme (also known as ADAM-17; MMP-1 stands for Fibroblast collagenase; MMP-2 stands for 72 kDa gelatinase (gelatinase A); MMP-3 stands for Stromelysin-1; MMP-8 stands for Neutrophil collagenase; MMP-9 stands for 92 kDa gelatinase (gelatinase B); and MMP-13 stands for collagenase-3.

TABLE 5

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 1 | 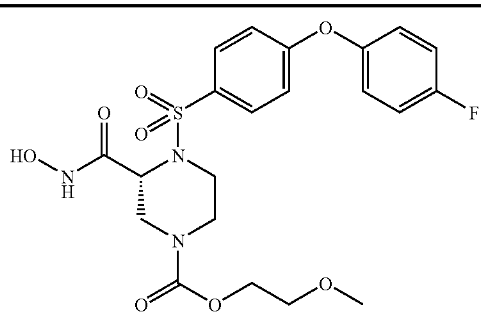 | A | | A | A | A | | | A |

TABLE 5-continued
| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 2 | 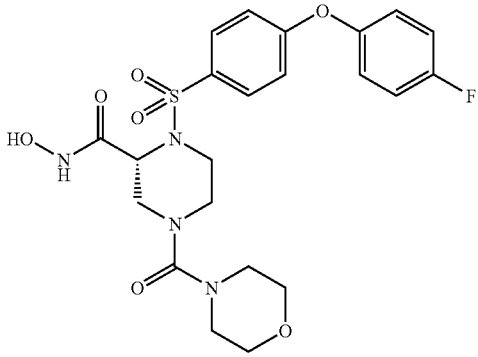 | A | | A | A | A | | | A |
| 3 | 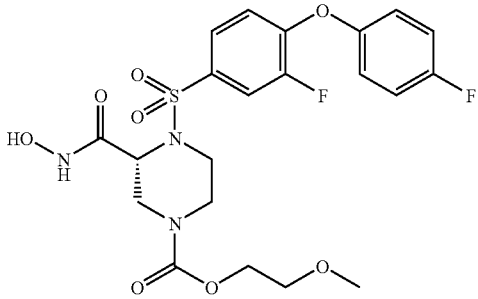 | A | | B | A | C | | | A |
| 4 | 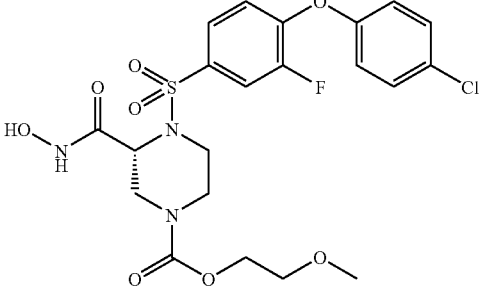 | A | | B | A | A | | | A |
| 5 | 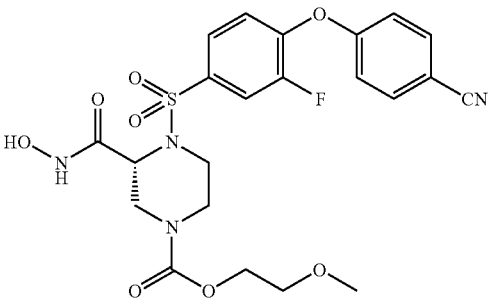 | A | | B | A | B | | | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 6 | 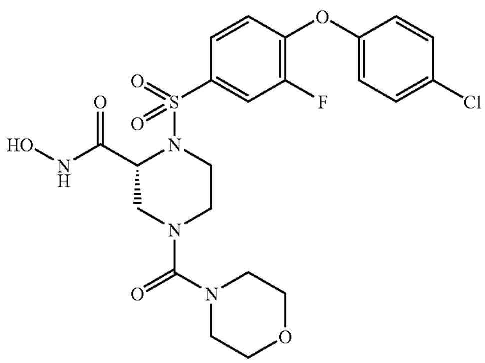 | A | | B | A | A | | | A |
| 7 | 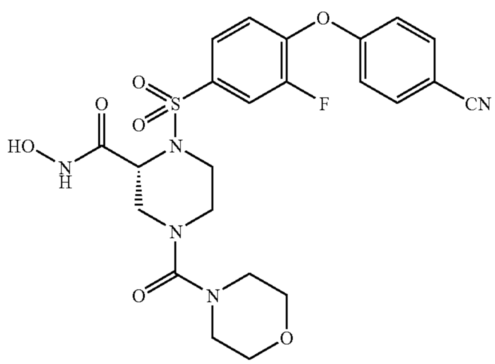 | A | | B | A | A | | | A |
| 8 | 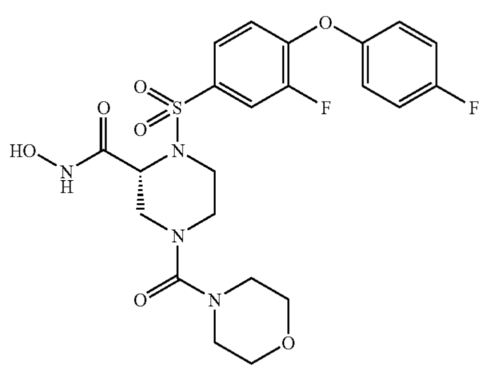 | A | | B | A | A | | | A |
| 9 | 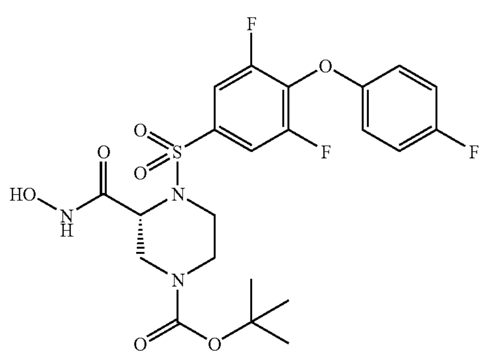 | A | | C | A | C | | | C |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 10 | 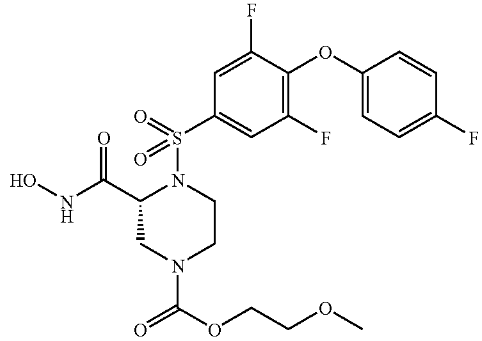 | A | | C | A | C | | | A |
| 11 | 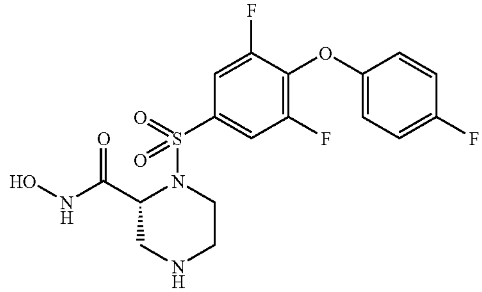 | B | | D | B | C | | | D |
| 12 | 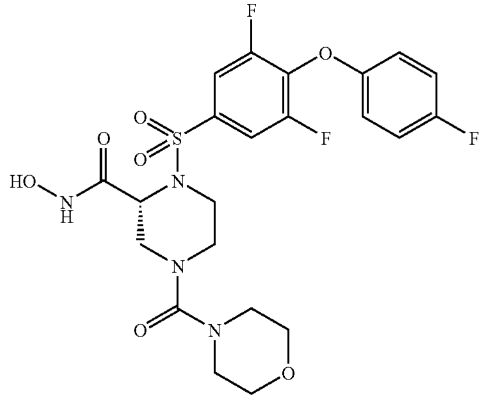 | A | | C | A | B | | | A |
| 13 | 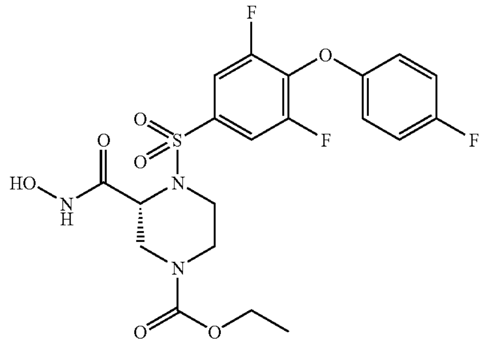 | A | | C | A | B | | | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 14 | 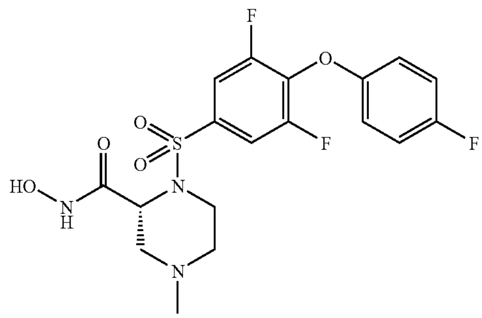 | B |  | D | A | D |  |  | A |
| 15 | 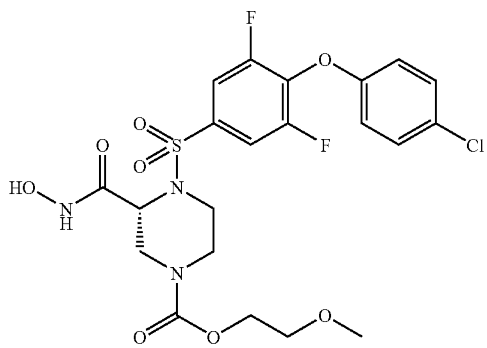 | A | B | C | A | B | A | A | A |
| 16 | 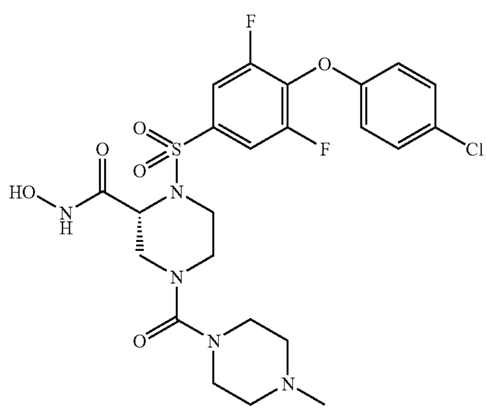 | A |  | D | A | C |  |  | A |
| 17 | 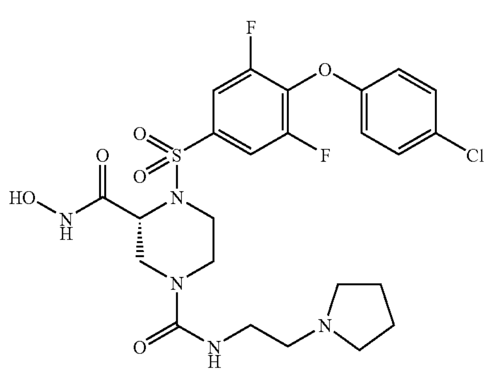 | A |  | C | A | B |  |  | A |

TABLE 5-continued
| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 18 | 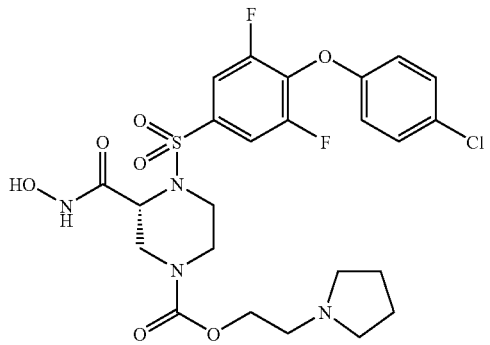 | A | | D | A | B | | | A |
| 19 | 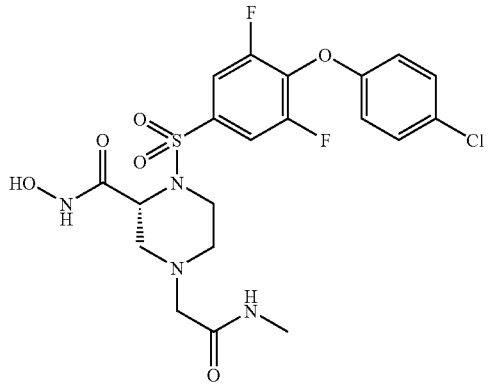 | A | | D | A | B | | | A |
| 20 | 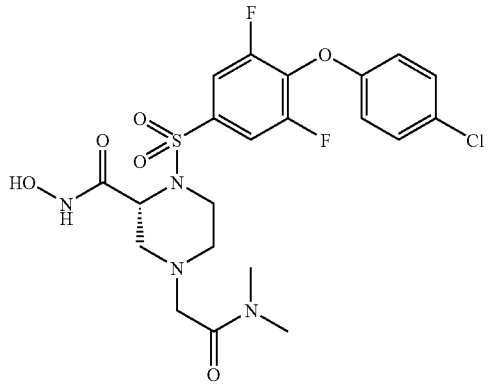 | A | | D | A | C | | | A |
| 21 | 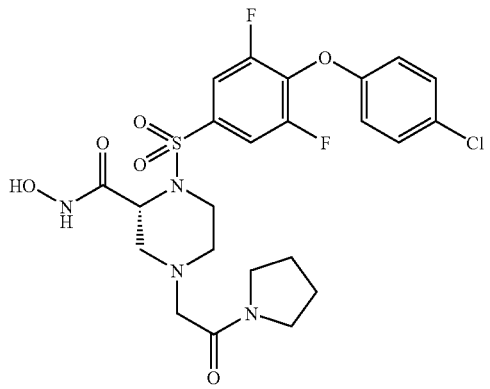 | A | | D | A | C | | | B |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 22 | 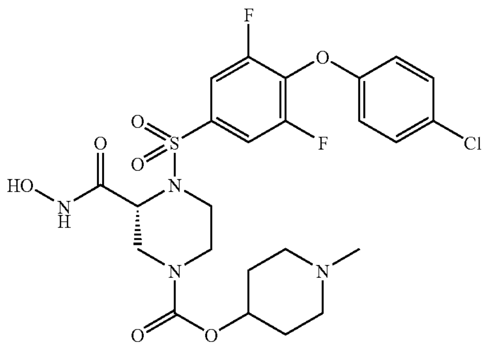 | A | | C | A | B | | | A |
| 23 | 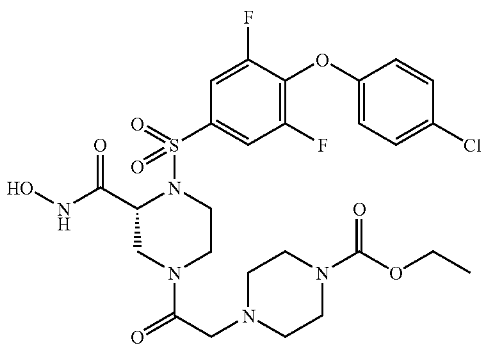 | A | | D | A | C | | | A |
| 24 | 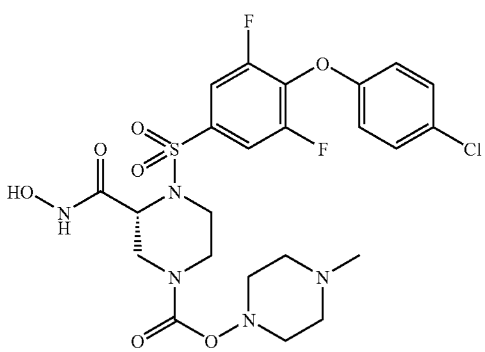 | A | | D | A | C | | | A |
| 25 | 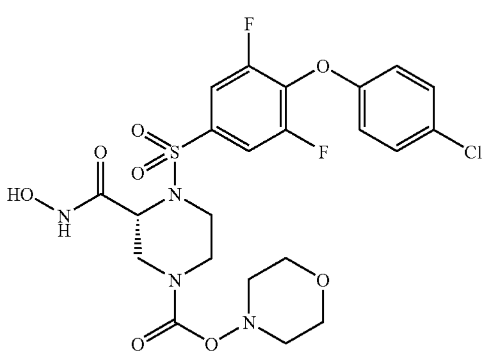 | A | | D | A | B | | | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 26 | 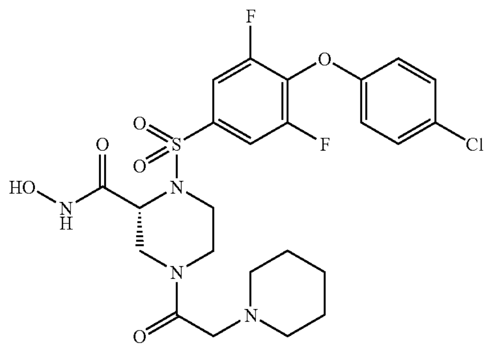 | A | D | A | C | | | | A |
| 27 | 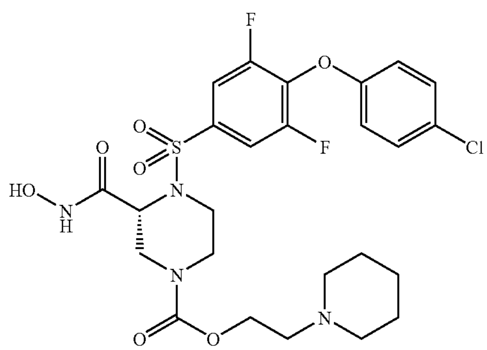 | A | | C | A | B | | | A |
| 28 | 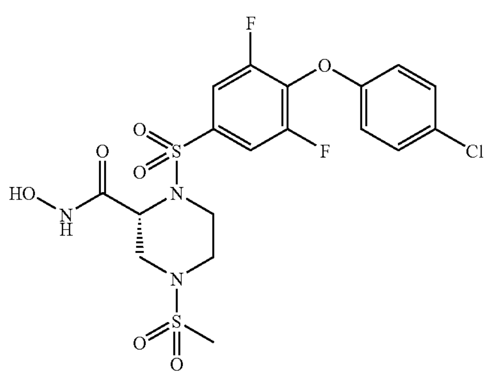 | A | | B | A | B | | | A |
| 29 | 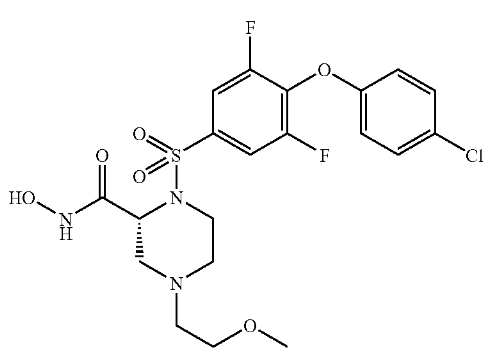 | A | | C | A | B | | | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 30 | 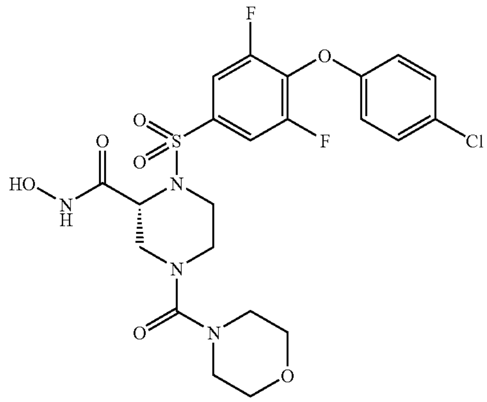 | A | B | C | A | B | A | B | A |
| 31 | 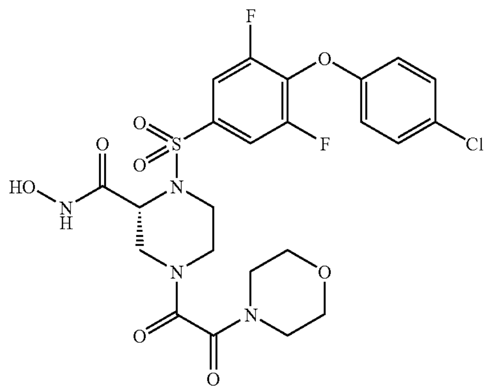 | A | B | C | A | B | | | A |
| 32 | 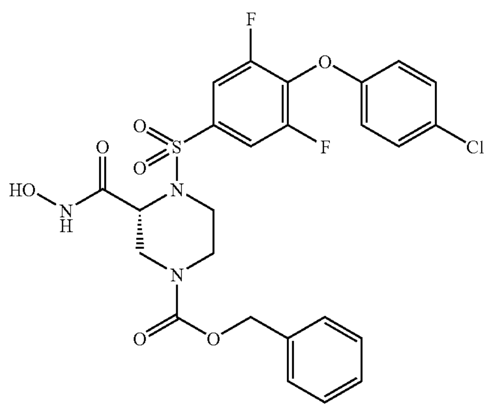 | A | | C | A | B | | | A |
| 33 | 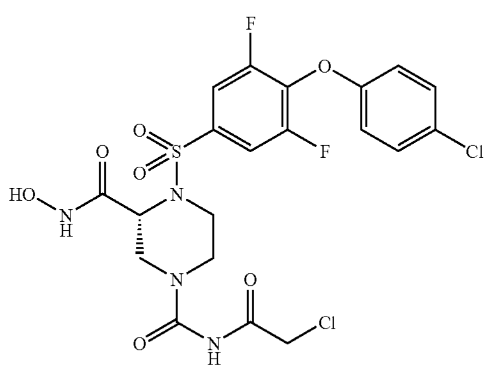 | A | | C | A | B | | | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 34 | 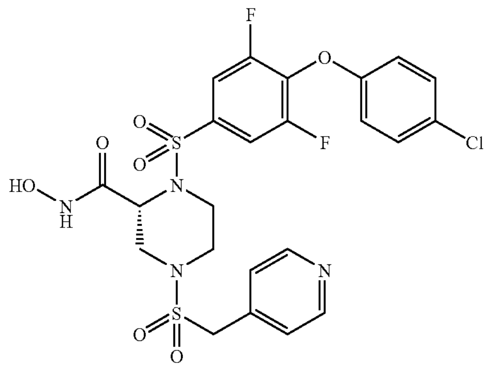 | A | A | C | A | B |  |  | A |
| 35 | 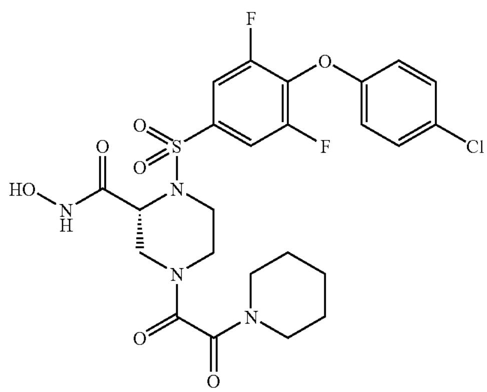 | A |  | C | A | B |  |  | A |
| 36 | 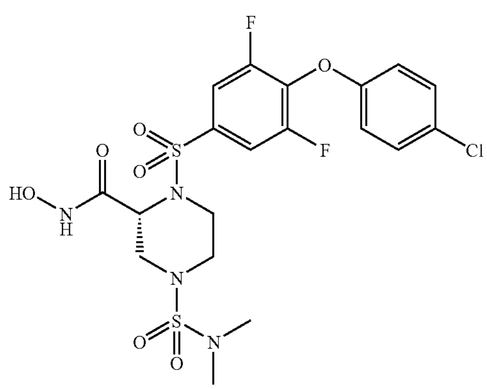 | A |  | C | A | B |  |  | A |
| 37 | 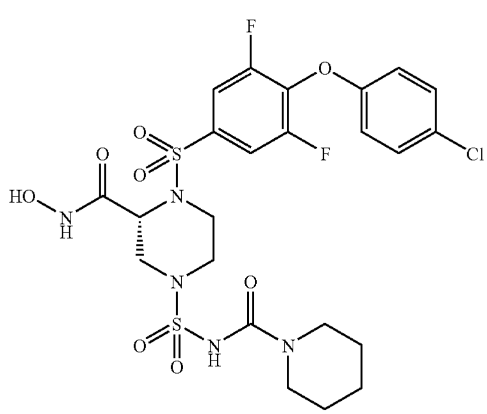 | A | B | C | A | A |  |  | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 38 | 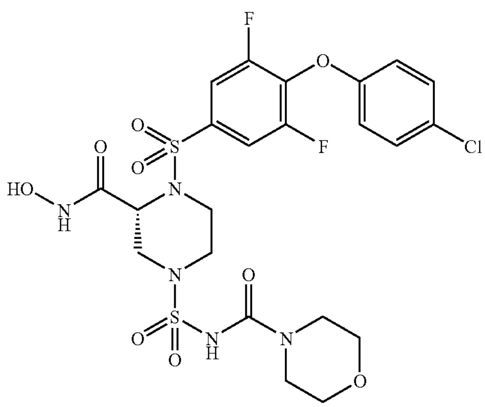 | A | B | C | A | A | | | A |
| 39 | 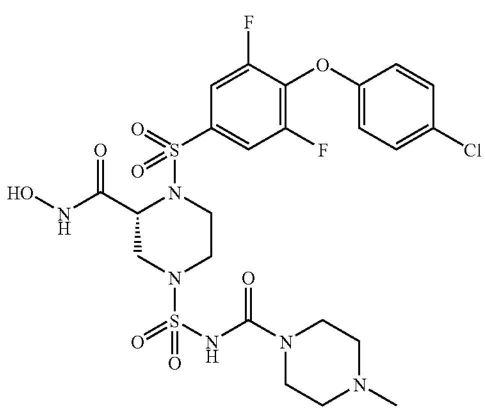 | A | | B | A | A | | | A |
| 40 | 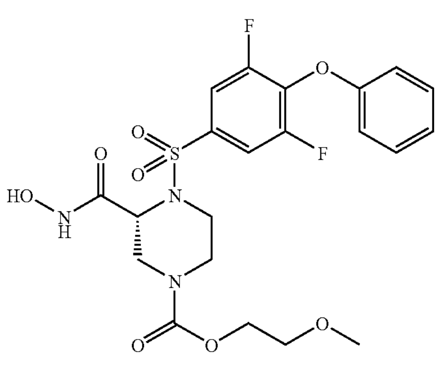 | A | | C | A | B | | | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 41 | 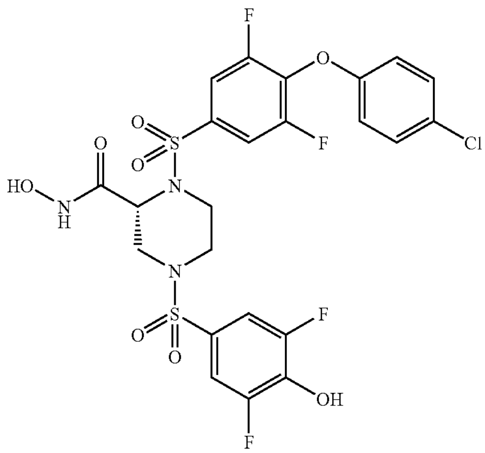 | A |  | C | A | A |  |  | A |
| 42 | 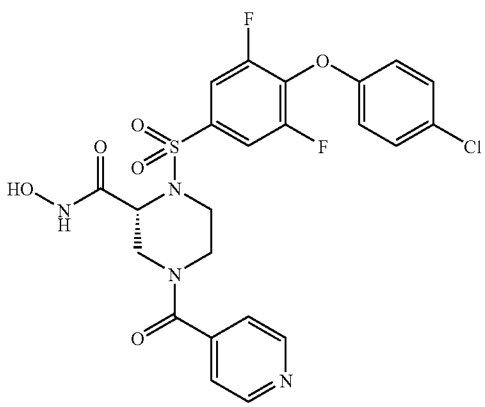 | A |  | C | A | C |  |  | A |
| 43 | 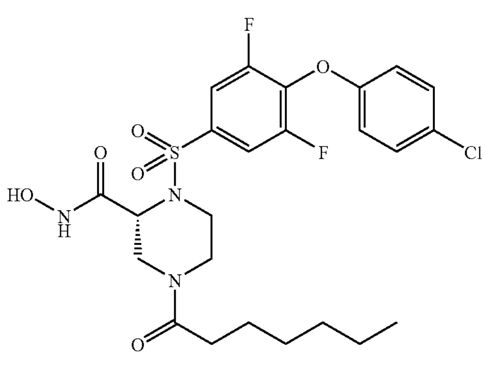 | A |  | D | A | B |  |  | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 44 | 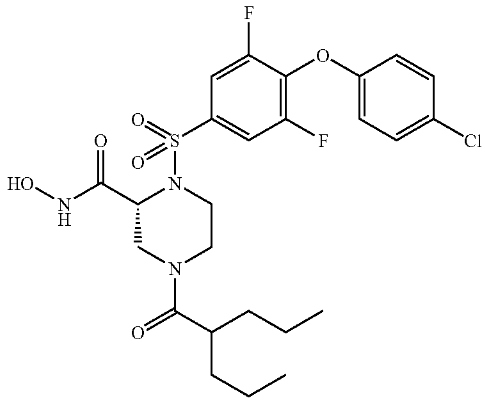 | A | | D | A | C | | | B |
| 45 | 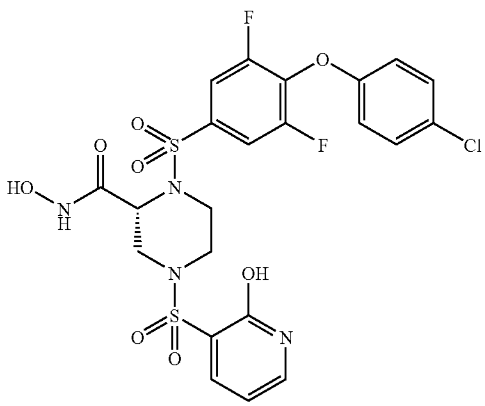 | A | B | C | A | B | | | A |
| 46 | 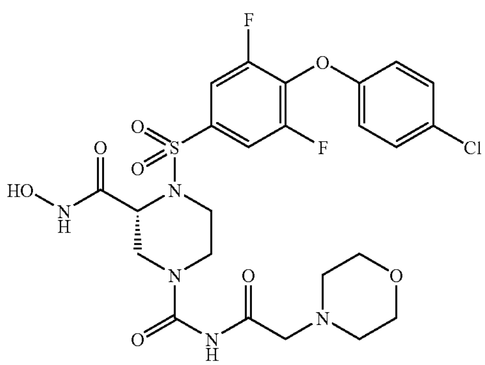 | A | | C | A | B | | | A |
| 47 | 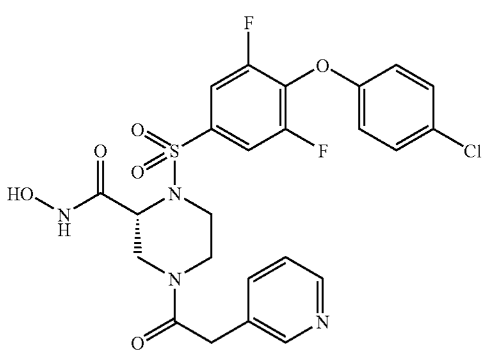 | A | | D | A | B | | | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 48 | 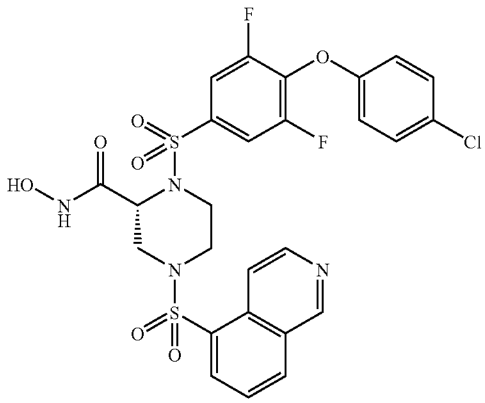 | A | | D | A | B | | | A |
| 49 | 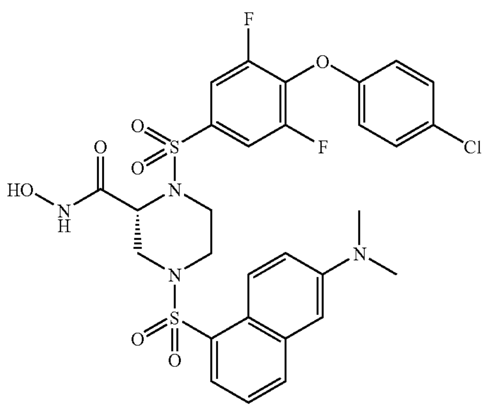 | C | | D | A | B | | | A |
| 50 | 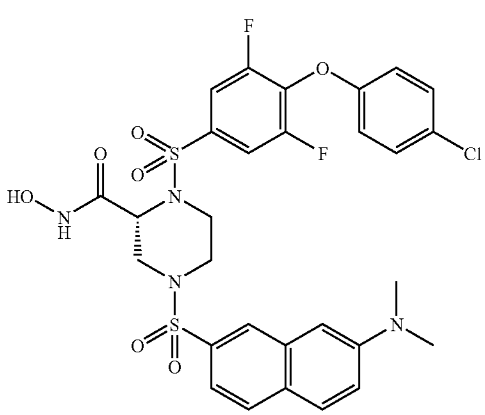 | C | | D | D | B | | | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 51 | 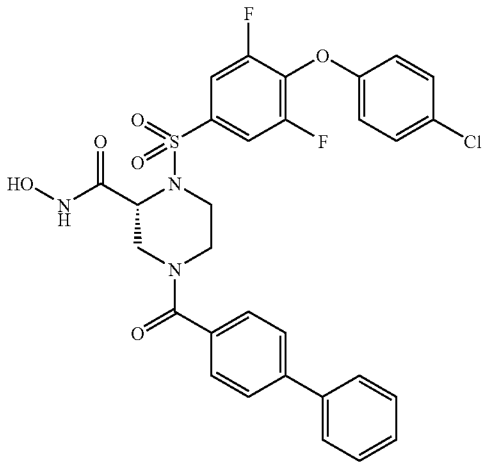 | B | | C | B | C | | | B |
| 52 | 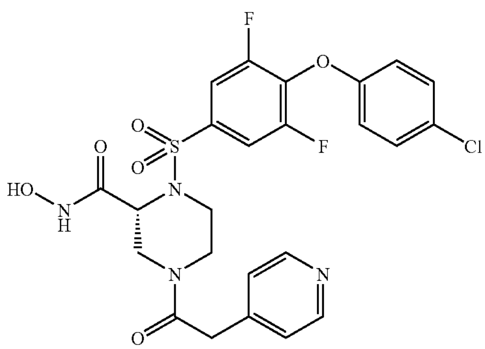 | A | | C | A | C | | | A |
| 53 | 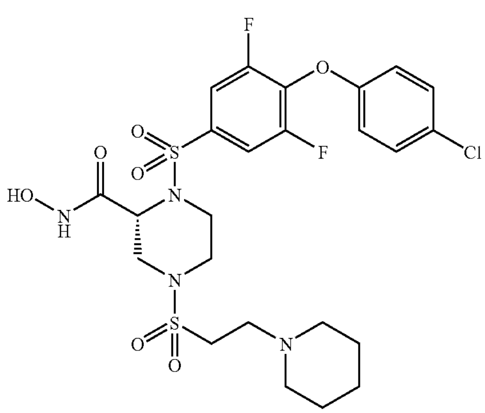 | A | | B | A | B | | | A |

TABLE 5-continued
| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 54 | 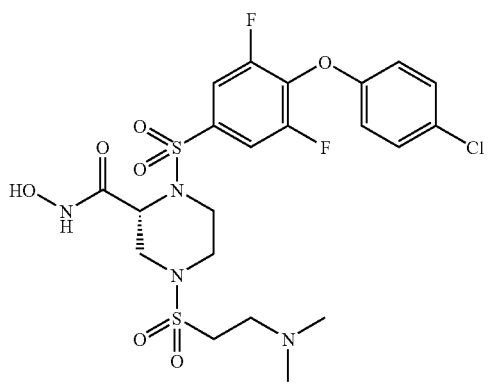 | A | A | B | A | A | | | A |
| 55 | 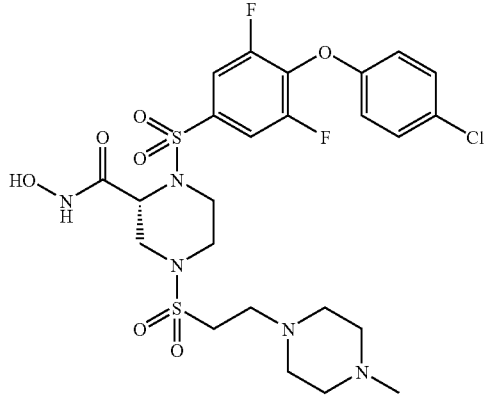 | A | | C | A | B | | | A |
| 56 | 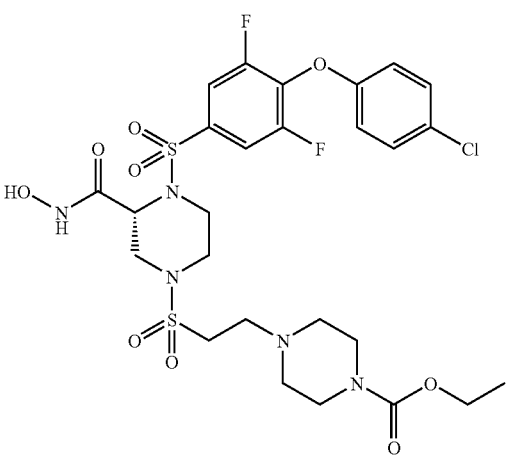 | A | | C | A | B | | | A |

TABLE 5-continued
| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 57 | 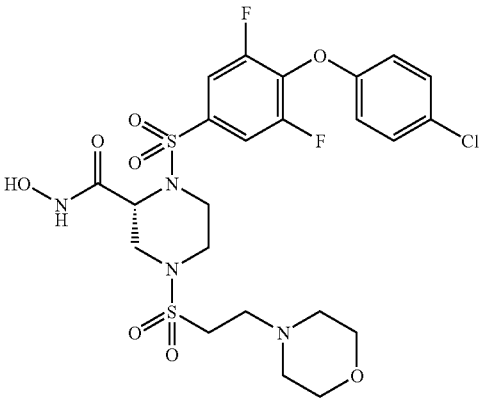 | B | | D | B | C | | | B |
| 58 | 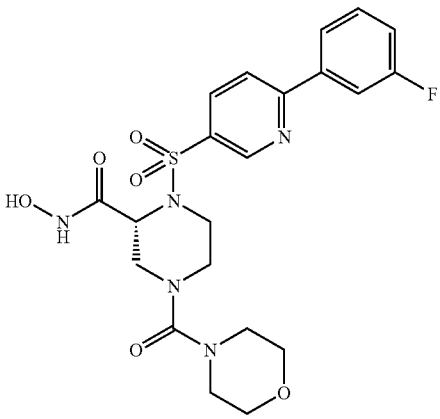 | A | | B | A | B | | | A |
| 59 | 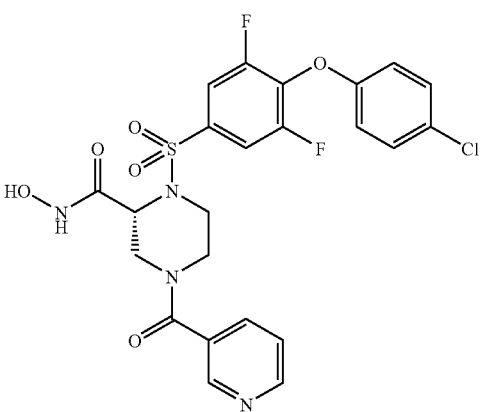 | A | | B | C | A | | B | A |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 60 | 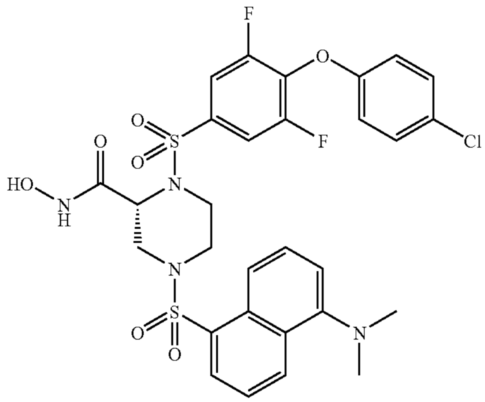 | B | | | D | A | C | | A |
| 61 | 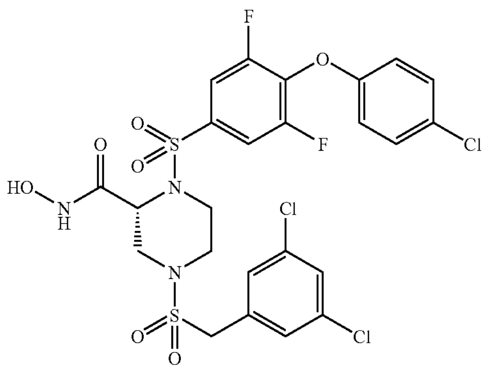 | B | | | D | C | D | | C |
| 62 | 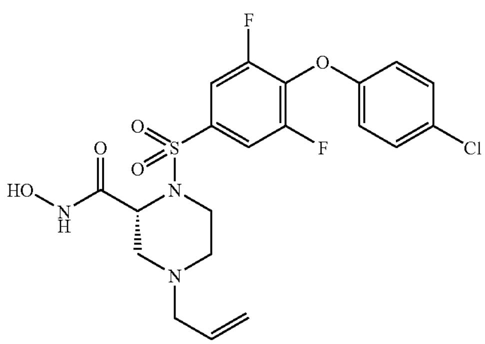 | B | | | D | A | C | | A |
| 63 | 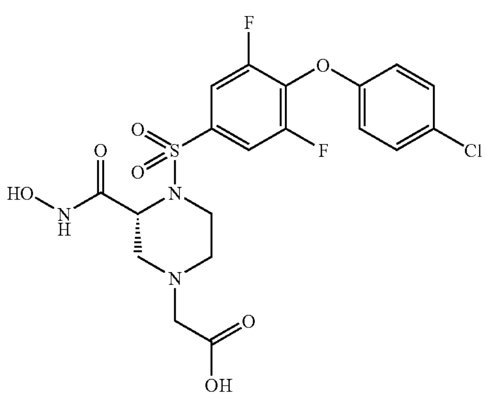 | B | | | D | B | C | | B |

TABLE 5-continued

| ENTRY | STRUCTURE | ADAM-10 IC$_{50}$ | TACE IC$_{50}$ | MMP-1 IC$_{50}$ | MMP-2 IC$_{50}$ | MMP-3 IC$_{50}$ | MMP-8 IC$_{50}$ | MMP-9 IC$_{50}$ | MMP-13 IC$_{50}$ |
|---|---|---|---|---|---|---|---|---|---|
| 64 | 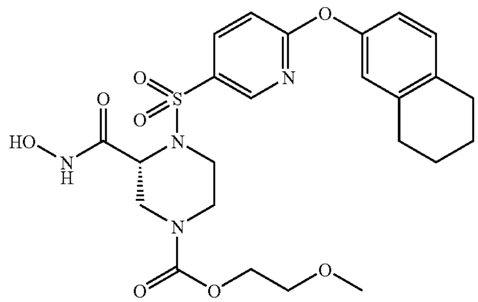 | A | B | | A | A | | | A |
| 65 | 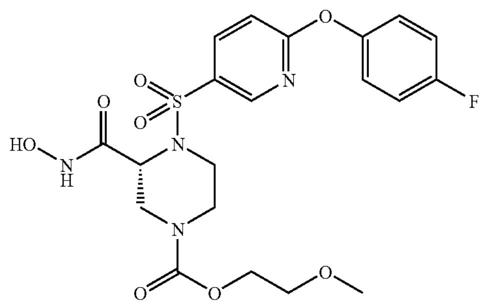 | B | | A | A | A | | | A |
| 66 | 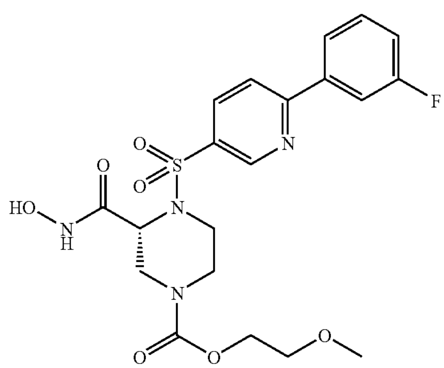 | A | B | | A | A | | | A |

Table 6 contains physical characterization data for selected compounds of the invention. $^1$H-NMR data were taken with a Varian AS400 Spectrometer (400 MHz, available from Varian GmbH, Darmstadt, Germany). The entry numbers in Table 6 correspond to those of Table 5 (and their corresponding structures).

TABLE 6

| Entry | $^1$H NMR Data (or MS data) |
|---|---|
| 1 | (CD3OD): 7.68 (d, 2H), 7.18-7.14 (m, 4H), 7.05 (d, 2H), 4.32 (m 1H), 4.23 (d, 1H), 4.15 (m, 2H), 4.00 (d, 1H), 3.68-3.64 (m, 2H), 3.55 (m, 2H), 3.35 (s, 3H), 3.2 (m, 1H), 3.00 (m, 1H) ppm. |
| 2 | (CD3OD): 7.69 (d, 2H, J = 9.2 Hz), 7.04 (m, 4H), 6.95 (d, 2H, J = 9.2 Hz), 4.30 (m, 1H), 3.76 (m, 1H), 3.50 (m, 7H), 3.10 (m, 4H), 2.90 (dd, 1H, J = 13.2, 4.4 Hz), 2.72 (m, 1H) ppm. |
| 3 | (CD3OD): 7.68 (dd, 1H), 7.55 (dd, 1H), 7.15-7.10 (m, 4H), 7.04 (dd, 1H), 4.28-4.12 (m, 2H), 4.15-4.00 (m, 3H), 3.70-3.65 (m, 2H), 3.55-3.50 (m, 2H), 3.33 (s, 3H), 3.22 (m, 1H), 3.03 (m, 1H) ppm. |
| 4 | (CD3OD): 7.68 (dd, 1H), 7.57 (dd, 1H), 7.38 (d, 2H), 7.13 (t, 1H), 7.08 (d, 1H), 4.28-4.12 (m, 2H), 4.15-4.00 (m, 3H), 3.70-3.65 (m, 2H), 3.55-3.50 (m, 2H), 3.33 (s, 3H), 3.22 (m, 1H), 3.03 (m, 1H) ppm. |
| 5 | (CD3OD): 7.75-7.71 (m, 3H), 7.65 (dd, 1H), 7.33 (dd, 1H), 7.20 (d, 2H), 4.32-4.26 (m, 2H), 4.16-4.05 (m, 3H), 3.81-3.75 (m, 2H), 3.56 (m, 2H), 3.34 (s, 3H), 3.27 (m, 1H), 3.06 (m, 1H) ppm. |

TABLE 6-continued

| Entry | $^1$H NMR Data (or MS data) |
|---|---|
| 6 | (CDCl3): 7.73 (d, 1H), 7.61 (d, 1H), 7.34 (d, 2H, J = 8.8 Hz), 6.99 (d, 2H, J = 8.8 Hz), 6.98 (m, 1H), 4.67 (s, 1H), 4.23 (d, 1H), 3.64 (m, 5H), 3.44 (d, 1H), 3.35 (m, 2H), 3.21 (m, 2H), 3.10 (m, 4H) ppm. |
| 7 | (CD3OD): 7.68-7.64 (m, 3H), 7.58 (d, 1H), 7.22 (t, 1H), 7.08 (d, 2H), 4.30 (m, 1H), 3.78 (d, 1H), 3.75-3.48 (m, 7H), 3.08-3.00 (m, 5H), 2.81 (m, 1H) ppm. |
| 8 | (CD3OD): 7.75 (d, 1H), 7.60 (d, 1H), 7.18-7.14 (m, 4H), 7.07 (t, 1H), 4.4 (m, 1H), 3.86 (d, 1H), 3.78-3.55 (m, 7H), 3.24-3.14 (m, 4H), 3.08 (dd, 1H), 2.87 (m, 1H) ppm. |
| 9 | (CD3OD): 7.60-7.58 (m, 2H), 7.08-7.00 (m, 4H), 4.3-4.2 (m, 2H), 4.08-4.02 (m, 1H), 3.75-3.70 (m, 2H), 3.23-3.18 (m, 1H), 3.12-2.90 (m, 1H) ppm |
| 10 | (CD3OD): 7.49 (d, 2H), 7.08-7.00 (m, 4H), 4.3-4.2 (m, 2H), 4.18-4.05 (m, 3H), 3.75-3.70 (m, 2H), 3.55-3.50 (m, 2H), 3.33 (s, 3H), 3.33-3.25 (m, 1H), 3.15-3.00 (m, 1H) ppm. |
| 11 | (CD3OD): 7.65 (d, 2H), 7.08-6.98 (m, 4H), 4.58 (d, 1H), 4.05 (dd, 1H), 3.81 (ddd, 1H), 3.63 (d, 1H), 3.46 (d, 1H), 3.35 (dd, 1H), 3.18 (ddd, 1H) ppm. |
| 12 | (CD3OD): 7.62 (m, 2H), 7.08-7.00 (m, 4H), 4.40 (s, 1H), 3.86 (d, 1H), 3.80-3.74 (m, 2H), 3.65-3.58 (m, 5H), 3.25-3.12 (m, 5H), 2.96 (m, 1H) ppm. |
| 13 | (CD3OD): 7.60-7.58 (m, 2H), 7.08-7.00 (m, 4H), 4.3-4.2 (m, 2H), 4.08-4.02 (m, 3H), 3.75-3.70 (m, 2H), 3.27 (m, 1H), 3.05 (m, 1H) ppm. |
| 14 | (CD3OD): 7.65-7.62 (m, 2H), 7.08-7.00 (m, 4H), 4.45 (s, 1H), 3.80 (d, 1H), 3.52 (t, 1H), 3.10 (d, 1H), 2.72 (d, 1H), 2.21 (s, 3), 2.16 (d, 1H), 1.96 (t, 1H) ppm. |
| 15 | (CD3OD): 7.60 (d, 2H), 7.32 (d, 2H), 7.03 (d, 2H), 4.32-4.26 (m, 2H), 4.16-4.05 (m, 3H), 3.81-3.75 (m, 2H), 3.56 (m, 2H), 3.34 (s, 3H), 3.27 (m, 1H), 3.06 (m, 1H) ppm. |
| 16 | MS: Calculated for C23H26ClF2N5O6S: 573.13; Found: 574.72 (M + 1). |
| 17 | (CD3OD): 7.60 (d, 2H, J = 7.2 Hz), 7.32 (d, 2H, J = 8.8 Hz), 6.98 (d, 2H, J = 9.2 Hz), 4.21 (m, 2H), 4.08 (m, 1H), 3.80-3.60 (m, 5H), 3.40 (m, 1H), 3.23 (m, 2H), 3.04 (m, 3H), 2.21 (m, 1H), 2.50-1.50 (m, 4H) ppm. |
| 18 | (CD3OD): 7.51 (d, 2H, J = 7.6 Hz), 7.23 (d, 2H, J = 6.4 Hz), 6.88 (d, 2H, J = 6.4 Hz), 4.19-4.11 (m, 2H), 3.98-3.94 (m, 1H), 3.73-3.67 (m, 4H), 3.59 (m, 1H), 3.50-3.14 (m, 5H), 3.03-2.91 (m, 3H), 1.99-1.88 (m, 4H) ppm. |
| 19 | (CD3OD): 7.82 (br. s, 1H), 7.69 (d, 2H), 7.38 (d, 2H), 7.05 (d, 2H), 4.58 (br s, 1H), 3.88 (m, 1H), 3.60 (td, 1H), 3.19-2.91 (m, 4H), 2.85-2.70 (m, 6H), 2.40-2.29 (m, 2H) ppm. |
| 20 | (CD3OD): 7.71 (d, 2H), 7.35 (d, 2H), 7.00 (d, 2H), 4.58 (br s, 1H), 3.80 (m, 1H), 3.40-3.33 (m, 2H), 3.30-3.20 (m, 2H), 3.05 (s, 3H), 2.96 (s, 3H), 2.81 (m, 1H), 2.40-2.30 (m, 2H) ppm. |
| 21 | DMSO-d$_6$: 9.8 (br, 1H), 9.0 (br, 1H), 7.85 (m, 2H), 7.4 (m, 2H), 7.1 (m, 2H), 4.4 (m, 3H), 3.6 (m, 7H), 3.0 (m, 3H), 2.0 (m, 4H). |
| 22 | (CD3OD): 7.61 (m, 2H), 7.32 (d, 2H, J = 8.8 Hz), 6.99 (d, 2H, J = 8.8 Hz), 4.40-4.20 (m, 4H), 4.10 (m, 1H), 3.80-3.60 (m, 4H), 3.50 (m, 1H), 3.40-3.15 (m, 4H), 2.89 (d, 3H), 2.15-2.00 (m, 2H) ppm. |
| 23 | DMSO-d$_6$: 10.2 (br, 1H), 9.0 (br, 1H), 7.8 (m, 2H), 7.4 (m, 2H), 7.1 (m, 2H), 4.4 (m, 4H), 4.0 (m, 7H), 3.3 (m, 8H), 1.2 (t, 3H). |
| 24 | DMSO-d$_6$: 7.8 (m, 2H), 7.4 (m, 2H), 7.1 (m, 2H), 3.8 (m, 11H), 3.4 (m, 2H), 3.0 (m, 4H), 2.8 (3, 3H). |
| 25 | DMSO-d$_6$: 10.2 (br, 1H), 9.0 (br, 1H), 7.8 (m, 2H), 7.45 (m, 2H), 7.2 (m, 2H), 4.4 (m, 4H), 3.8 (m, 7H), 3.4 (m, 6H). |
| 26 | DMSO-d$_6$: 9.4 (br, 1H), 9.0 (br, 1H), 7.8 (m, 2H), 7.4 (m, 2H), 7.1 (m, 2H), 4.85 (m, 1H), 4.1 (m, 2H), 3.0 (m, 6H), 3.4 (m, 4H), 3.0 (m, 2H), 1.9 (m, 4H). |
| 27 | (CD3OD): 7.54 (d, 2H, J = 7.2 Hz), 7.25 (d, 2H, J = 8.8 Hz), 6.89 (d, 2H, J = 8.8 Hz), 4.15 (m, 3H), 3.90 (m, 1H), 3.78 (m, 1H), 3.60 (m, 2H), 3.40-3.20 (m, 4H), 3.05 (m, 1H), 3.00 (m, 1H), 2.80 (m, 1H), 2.70 (m, 1H), 1.80-1.60 (m, 4H), 1.40 (m, 1H) ppm. |
| 28 | (CDCl3): 9.20 (br s, 1H), 7.58 (d, 2H), 7.30 (d, 2H), 6.90 (d, 2H), 4.65 (br s, 1H), 4.19 (d, 1H), 3.95-3.60 (m, 2H), 3.33 (m, 1H), 3.15-2.80 (m, 2H), 2.88 (s, 3H) ppm. |
| 29 | (CDCl3): 7.61 (d, 2H), 7.29 (d, 2H), 6.90 (d, 2H), 4.71 (br s, 1H), 3.75 (br d, 1H), 3.60-3.48 (m, 2H), 3.42 (s, 3H), 3.20 (d, 1H), 3.09 (td, 1H), 2.88 (br d, 1H), 2.75 (m, 1H), 2.60-2.49 (m, 3H) ppm. |
| 30 | (CDCl3): 11.8 (br. S, 1H), 7.61 (d, 2H), 7.55 (br. s, 1H), 7.26 (d, 2H), 6.90 (d, 2H), 4.71 (s, 1H), 4.28 (d, 1H), 3.70-3.62 (m, 4H), 3.48 (d, 1H), 3.36-3.16 (m, 5H), 3.00 (t, 1H) ppm. |
| 31 | (CDCl3): 11.23 (br s, 1H), 7.59 (d, 2H), 7.26 (d, 2H), 6.95 (d, 2H), 4.70 (br s, 1H), 3.40 (br d, 1H), 4.23 (d, 1H), 3.85-3.38 (m, 10H), 3.20-2.90 (m, 2H) ppm. |
| 32 | (CDCl3): 7.46 (d, 2H, J = 6.8 Hz), 7.26 (m, 4H), 6.91 (d, 2H, J = 9.2 Hz), 4.60 (s, 1H), 4.00 (m, 1H), 3.80 (m, 2H), 3.60 (m, 2H), 3.40 (m, 1H), 2.60 (m, 2H) ppm. |
| 33 | (CDCl3): 7.54 (d, 2H, J = 5.6 Hz), 7.25 (d, 2H, J = 9.2 Hz), 6.86 (d, 2H, J = 9.2 Hz), 4.60 (m, 1H), 4.40 (m, 2H), 4.05 (m, 1H), 3.75 (m, 2H), 3.45 (m, 1H), 3.0 (m, 1H), 2.93 (s, 2H) ppm. |
| 34 | (CD3OD): 8.61 (br. s, 1H), 7.75 (m, 2H), 7.67 (d, 2H), 7.33 (d, 2H), 7.03 (d, 2H), 4.54 (m, 1H), 4.03-3.88 (m, 3H), 3.60 (m, 2H), 3.12 (m, 1H), 2.93 (m, 1H) ppm. |
| 35 | (CDCl3): 7.63 (d, 1H), 7.49 (d, 1H), 7.28 (m, 2H), 6.90 (dd, 2H), 4.51 (m, 1H), 4.42 (m, 1H), 4.14 (br d, 1H), 3.82-2.91 (m, 8H), 1.84-1.45 (m, 6H) ppm. |
| 36 | (CDCl3): 7.54 (d, 2H, J = 6.4 Hz), 7.30 (d, 2H, J = 8.8 Hz), 6.91 (d, 2H, J = 8.8 Hz), 4.70 (m, 1H), 4.10 (m, 1H), 3.90 (m, 1H), 3.60 (m, 1H), 3.40 (m, 1H), 2.83 (s, 6H), 2.80 (m, 2H) ppm. |
| 37 | (CD3OD): 7.65 (d, 2H), 7.31 (d, 2H), 7.00 (d, 2H), 4.60 (m, 1H), 4.00 (m, 2H), 3.69 (m, 2H), 3.40-3.00 (m, 5H), 2.82 (m, 1H), 1.70-1.40 (m, 6H) ppm. |
| 38 | (CD3OD): 7.69 (d, 2H), 7.33 (d, 2H), 7.00 (d, 2H), 4.60 (br s, 1H), 3.92 (br t, 2H), 3.62-3.41 (m, 10H), 2.90 (dd, 1H), 2.70 (td, 1H) ppm. |
| 39 | (CD3OD): 7.65 (d, 2H), 7.33 (d, 2H), 7.00 (d, 2H), 4.59 (br s, 1H), 3.88 (m, 2H), 3.70-3.15 (m, 5H), 2.90-2.45 (m, 6H) ppm. |

TABLE 6-continued

| Entry | ¹H NMR Data (or MS data) |
|---|---|
| 40 | (CD3OD): 7.48 (d, 2H), 7.22 (dd, 2H), 6.99 (t, 1H), 6.89 (d, 2H), 4.23-4.15 (m, 2H), 4.05-3.95 (m, 3H), 3.67-3.64 (m, 2H), 3.45 (m, 2H), 3.25 (s, 3H), 3.2 (m, 1H), 3.00 (m, 1H) ppm. |
| 41 | (CDCl3): 7.46 (d, 2H, J = 6.8 Hz), 7.26 (m, 4H), 6.91 (d, 2H, J = 9.2 Hz), 4.60 (s, 1H), 4.00 (m, 1H), 3.80 (m, 2H), 3.60 (m, 2H), 3.40 (m, 1H), 2.60 (m, 2H) ppm. |
| 42 | (CD3OD): 8.79 (br. s, 2H), 7.70 (m, 4H), 7.38 (d, 2H), 7.00 (d, 2H), 4.40 (m, 2H), 4.00-3.00 (m, 5H) ppm. |
| 43 | (CDCl3): 7.50 (d, 2H), 7.23 (m, 2H), 6.87 (d, 2H), 4.86 (d, 1H), 4.57 (d, 1H), 4.05 (m, 2H), 3.38 (m, 2H), 3.04 (m, 1H), 2.31 (t, 2H), 1.53 (s, 2H), 1.25 (s, 6H), 0.85 (t, 3H) ppm. |
| 44 | (CDCl3): 7.52 (d, 2H, J = 6.4 Hz), 7.24 (d, 2H, J = 8.8 Hz), 6.87 (d, 2H, J = 8.4 Hz), 4.97 (d, 1H), 4.71 (s, 1H), 4.05 (d, 1H), 3.80 (d, 1H), 3.37 (m, 1H), 3.26 (t, 1H), 3.05 (d, 1H), 2.62 (m, 1H), 1.54 (m, 2H), 1.80 (m, 2H), 1.18 (m, 4H), 0.85 (dt, 6H) ppm. |
| 45 | (CDCl3): 8.15 (s, 1H), 7.65 (s, 1H), 7.47 (m, 2H), 7.21 (d, 2H, J = 8.8 Hz), 6.84 (d, 2H, J = 8.4 Hz), 6.43 (s, 1H), 4.63 (s, 1H), 3.60 (m, 3H), 2.80 (m, 2H) ppm. |
| 46 | MS: Calculated for C24H26ClF2N5O8S: 617.12; Found: LC/MS: 618.2 (M + 1). |
| 47 | (CD3OD): 8.60 (m, 2H), 8.25 (d, 1H), 7.83 (m, 1H), 7.62-7.50 (m, 2H), 7.22 (m, 2H), 6.85 (m, 2H), 4.60-4.20 (m, 2H), 4.15-3.95 (m, 2H), 3.85-3.65 (m, 2H), 3.50-3.40 (m, 2H), 3.10 (m, 1H) ppm. |
| 48 | (CD3OD): 9.60 (br s, 1H), 8.60 (m, 4H), 7.95 (t, 1H), 7.60 (d, 2H), 7.37 (d, 2H), 7.00 (d, 2H), 4.60 (br s, 1H), 4.15 (br d, 1H), 3.93 (br d, 1H), 3.71-3.42 (m, 2H), 2.80-2.50 (m, 2H) ppm. |
| 49 | (CD3OD): 8.50 (d, 1H), 7.99 (d, 1H), 7.79 (d, 1H), 7.58 (m, 2H), 7.40 (m, 4H), 7.11 (m, 3H), 4.60 (br s, 1H), 4.20 (br d, 1H), 3.85 (br d, 1H), 3.49 (m, 2H), 3.09 (s, 6H), 2.50 (dd, 1H), 2.30 (td, 1H) ppm. |
| 50 | (CD3OD): 8.09 (s, 1H), 7.80 (dd, 2H), 7.60-7.42 (m, 3H), 7.31 (m, 3H), 7.95 (m, 3H), 4.60 (br s, 1H), 4.08 (m, 1H), 3.91 (br d, 1H), 3.60 (m, 2H), 3.10 (s, 6H), 2.42 (dd, 1H), 2.22 (td, 1H) ppm. |
| 51 | (CDCl3): 7.63 (d, 2H, J = 7.6 Hz), 7.56 (d, 2H, 7.2 Hz), 7.53-7.37 (m, 6H), 7.24 (m, 3H), 6.86 (d, 2H, J = 8.8 Hz), 3.90 (s, 1H), 3.70 (m, 2H), 3.45 (m, 1H), 3.30 (m, 3H) ppm. |
| 52 | (CD3OD): 8.45 (br s, 2H), 7.78 (d, 1H), 7.58 (m, 3H), 7.38 (m, 2H), 7.00 (m, 2H), 4.80-4.05 (m, 2H), 4.00-3.77 (m, 5H), 3.45-3.05 (m, 2H) ppm. |
| 53 | (CD3OD): 7.70 (d, 2H), 7.39 (d, 2H), 7.00 (d, 2H), 4.60 (br s, 1H), 4.00 (m, 2H), 3.79 (m, 2H), 4.60-3.40 (m, 6H), 3.20-2.90 (m, 4H), 2.00-1.40 (m, 6H) ppm. |
| 54 | (CD3OD): 7.70 (d, 2H), 7.39 (d, 2H), 7.00 (d, 2H), 4.60 (br s, 1H), 4.00 (m, 2H), 3.75 (m, 2H), 4.49 (m, 4H), 3.18 (m, 2H), 2.93 (s, 6H) ppm. |
| 55 | (CD3OD): 7.66 (d, 2H), 7.35 (d, 2H), 7.03 (d, 2H), 4.58 (m, 1H), 4.03-3.92 (m, 3H), 3.71-3.68 (m, 3H), 3.27-3.25 (t, 2H), 3.15-3.13 (m, 4H), 2.97-2.93 (m, 1H), 2.88 (s, 3H), 2.86-2.82 (m, 5H) ppm |
| 56 | (CD3OD): 7.68-7.66 (d, 2H), 7.35-7.33 (d, 2H), 7.04-7.01 (d, 2H), 4.57 (m, 1H), 4.13-4.08 (q, 2H), 4.02-3.98 (m, 1H), 3.71-3.68 (m, 2H), 3.46 (m, 4H), 3.26-3.23 (t, 2H), 3.19-3.15 (dd, 1H), 2.96-2.95 (m, 1H), 2.77-2.73 (m, 2H), 2.46 (m, 4H), 1.26-1.22 (t, 3H) ppm |
| 57 | (CD3OD): 7.19 (d, 2H), 7.14 (d, 2H), 6.83 (d, 2H), 4.48 (br s, 1H), 3.95-3.92 (br d, 1H), 3.83-3.80 (br d, 1H), 3.58-3.53 (m, 6H), 3.15 (dd, 2H), 2.94 (dd, 1H), 2.75-2.74 (td, 1H), 2.63-2.60 (t, 2H), 2.40-2.39 (m, 4H) ppm |
| 58 | (CD3OD): 9.00 (d, 1H), 8.23 (d, 1H), 8.07 (d, 1H), 7.92-7.86 (m, 2H), 7.52 (m, 1H), 7.22 (m, 1H), 4.50 (m, 1H), 3.90-3.57 (m, 8H), 3.22-3.08 (m, 5H), 2.97 (m, 1H) ppm. |
| 59 | (CD3OD): 8.54 (d, 2H), 7.77 (br s, 1H), 7.57-7.50 (m, 2H), 7.44-7.42 (m, 1H), 7.27-7.22 (m, 2H), 6.95-6.92 (m, 2H), 4.40-4.20 (m, 1H), 3.85-3.60 (m, 3H), 3.57-3.18 (m, 2H), 3.10-2.95 (m, 1H) ppm |
| 60 | MS: calculate for C29H27ClF2N4O7S2: 680.10; found: 681.20 (M + 1). |
| 61 | MS: calculated for C24H20Cl3F2N3O7S2: 668.98; found: 669.90 (M + 1). |
| 62 | (CD3OD): 7.63 (d, 2H, J = 7.2 Hz), 7.25 (d, 2H, J = 9.2 Hz), 6.93 (d, 2H, J = 9.2 Hz), 5.79 (m, 1H), 5.47 (s, 1H), 5.44 (d, 1H), 4.56 (d, 1H), 4.00 (d, 1H), 3.70-3.50 (m, 4H), 3.35 (d, 1H), 2.99 (d, 1H), 2.88 (t, 1H) ppm. |
| 63 | (CD3OD): 7.66 (d, 2H, J = 7.6 Hz), 7.35 (d, 2H, J = 8.8 Hz), 6.99 (d, 2H, J = 9.2 Hz), 3.85 (d, 1H), 3.67 (s, 2H), 3.61 (d, 1H), 3.44 (m, 2H), 3.04 (d, 1H), 2.83 (dd, 1H), 2.66 (dt, 1H) ppm. |
| 64 | (CD3OD): 8.45 (d, 1H), 8.10 (dd, 1H), 7.12 (d, 1H), 7.02 (d, 1H), 6.86-6.82 (m, 2H), 4.33-4.25 (m, 2H), 4.15-4.05 (m, 3H), 3.70-3.65 (m, 2H), 3.55 (m, 2H), 3.35 (s, 3H), 3.25 (m, 1H), 3.05 (m, 1H), 2.78 (m, 4H), 1.80 (m, 4H) ppm. |
| 65 | (CD3OD): 8.47 (d, 1H), 8.12 (dd, 1H), 7.22-7.09 (m, 5H), 4.33-4.25 (m, 2H), 4.15-4.05 (m, 3H), 3.70-3.65 (m, 2H), 3.55 (m, 2H), 3.33 (s, 3H), 3.25 (m, 1H), 3.05 (m, 1H) ppm. |
| 66 | (CD3OD): 9.96 (d, 1H), 8.20 (d, 1H), 8.14 (d, 1H), 7.90 (d, 1H), 7.86 (d, 1H), 7.50 (m, 1H), 7.21 (m, 1H), 4.40 (m, 1H), 4.28 (d, 1H), 4.12-4.05 (m, 3H), 3.75-3.70 (m, 2H), 3.52 (m, 2H), 3.30 (s, 3H), 3.25 (m, 1H), 3.06 (m, 1H) ppm. |

We claim:

1. A method of making a bis-aryl ether sulfonyl halide according to formula VII:

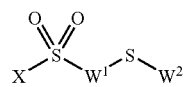

VII wherein X is a halide; and $W^1$ and $W^2$ are each independently an optionally substituted aryl, the method comprising: (a) combining a metal-aryloxide salt of a corresponding hydroxide-substituted aryl compound with a fluoro-substituted nitro aryl compound to make a bis-aryl ether nitro-aromatic compound; (b) reducing a nitro group of the bis-aryl ether nitro-aromatic compound to produce a corresponding aniline derivative; and (c) converting the corresponding aniline derivative to the bis-aryl ether sulfonyl halide.

2. The method of claim 1, wherein (a)-(c) are performed in the order described.

3. The method of claim 2, wherein the metal-aryloxide salt is combined with the fluoro-substituted nitro aryl in an organic solvent.

4. The method of claim 3, wherein the organic solvent comprises at least one of DMF and acetonitrile.

5. The method of claim 4, wherein the metal-aryloxide salt comprises at least one of a cesium salt and a potassium salt.

6. The method of claim 5, wherein the corresponding aniline derivative is converted to the bis-aryl ether sulfonyl halide via a diazonium intermediate of said corresponding aniline derivative.

7. The method of claim 6, wherein the fluoro-substituted nitro aryl compound is 3,4,5-trifluornitrobenzene.

8. The method of claim 7, wherein the metal-aryloxide salt is a cesium salt.

9. The method of claim 8, wherein the corresponding hydroxide-substituted aryl compound is 4-chlorophenol.

10. The method of claim 9, wherein the bis-aryl ether sulfonyl halide is 4-(4-chlorophenoxy)-3,5-difluorophenyl-sulfonyl chloride.

* * * * *